US012637446B2

(12) United States Patent
Janton et al.

(10) Patent No.: US 12,637,446 B2
(45) Date of Patent: May 26, 2026

(54) SOLID STATE FORMS OF ASCIMINIB AND PROCESSES FOR THE PREPARATION THEREOF

(71) Applicant: TAPI CZECH INDUSTRIES S.R.O., Opava-Komarov (CZ)

(72) Inventors: Nikolina Janton, Jakovlje (HR); Helena Ceric, Zagreb (HR)

(73) Assignee: TAPI CZECH INDUSTRIES S.R.O, Opava-Komarov (CZ)

( * ) Notice: Subject to any disclaimer, the term of this patent is extended or adjusted under 35 U.S.C. 154(b) by 888 days.

(21) Appl. No.: 17/795,056

(22) PCT Filed: Jan. 28, 2021

(86) PCT No.: PCT/US2021/015468
§ 371 (c)(1),
(2) Date: Jul. 25, 2022

(87) PCT Pub. No.: WO2021/154980
PCT Pub. Date: Aug. 5, 2021

(65) Prior Publication Data

US 2023/0097240 A1 Mar. 30, 2023

Related U.S. Application Data

(60) Provisional application No. 63/052,589, filed on Jul. 16, 2020, provisional application No. 63/035,933, filed on Jun. 8, 2020, provisional application No. 63/005,539, filed on Apr. 6, 2020, provisional application No. 62/966,625, filed on Jan. 28, 2020.

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC .......................... C07D 401/14; C07B 2200/13
See application file for complete search history.

(56) References Cited

U.S. PATENT DOCUMENTS 8,829,195 B2 * 9/2014 Dodd ................ A61K 31/4439 546/276.4

OTHER PUBLICATIONS

Brittain, "Polymorphism in Pharmaceutical Solids", 2009, Informa Healthcare USA, 2nd Ed., p. 318-346 (Year: 2009).*
Serajuddin, Abu T.M. "Salt formation to improve drug solubility", Advanced Drug Delivery Reviews, Elsevier, Amsterdam , NL, vol. 59, No. 7, Aug. 24, 2007 (Aug. 24, 2007), pp. 603-616, XP022211982.
Byrn, Stephen et al. "Pharmaceutical Solids: A Strategic Approach to Regulatory Considerations", Pharmaceutical Research, vol. 12, No. 7 , Jan. 1, 1995 (Jan. 1, 1995), pp. 945-954, XP055531015.
International Search Report and Written Opinion of the International Searching Authority issued in corresponding application PCT/US2021/015468 mailed May 28, 2021 (19 pages).

* cited by examiner

*Primary Examiner* — Brenda L Coleman
*Assistant Examiner* — Madeline E Braun
(74) *Attorney, Agent, or Firm* — Carter, DeLuca & Farrell, LLP

(57) ABSTRACT

The present disclosure encompasses solid state forms of Asciminib and salts thereof, in embodiments crystalline polymorphs of Asciminib and salts thereof, processes for preparation thereof, and pharmaceutical compositions thereof.

10 Claims, 22 Drawing Sheets

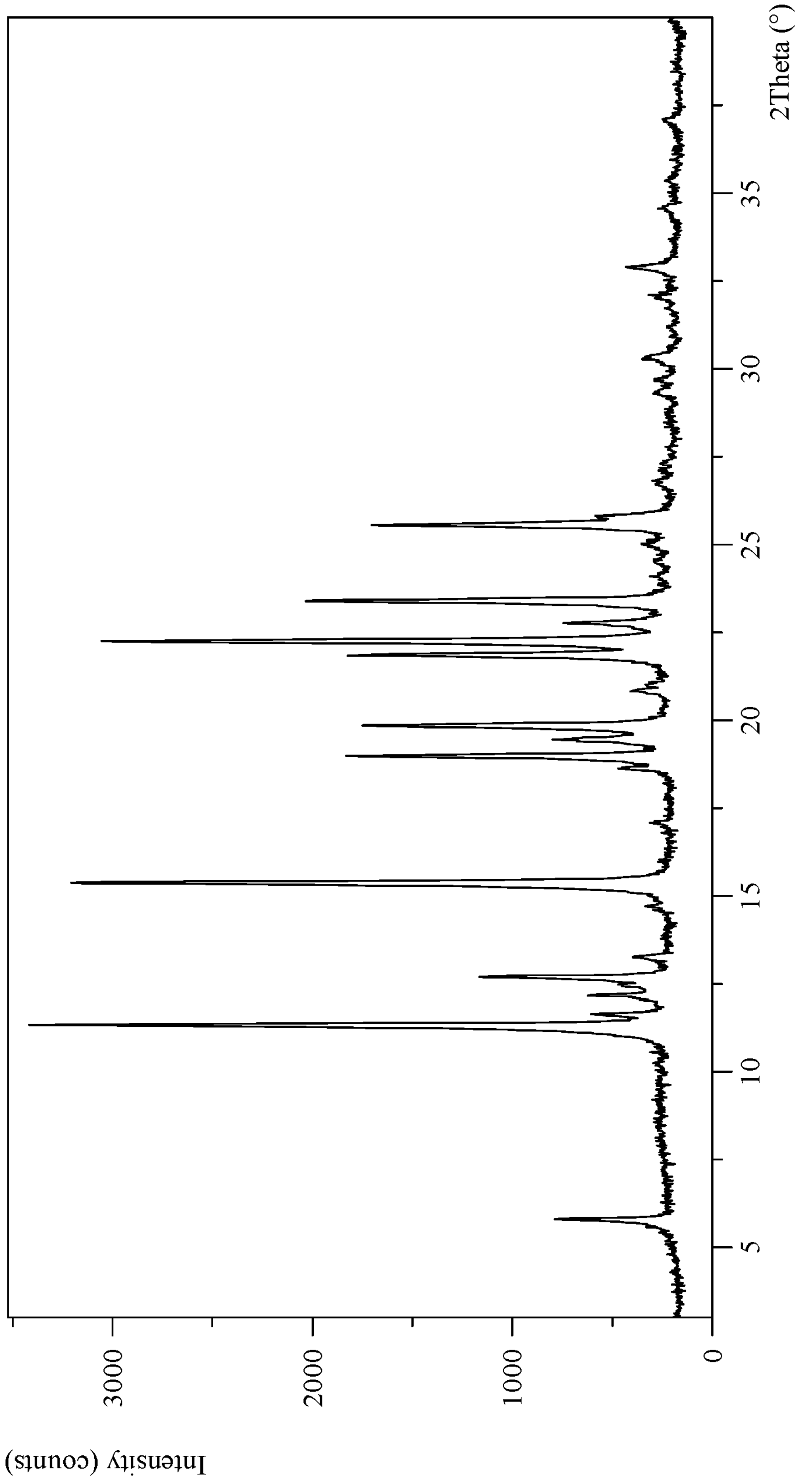
Figure 1. XRPD pattern of Asciminib, Form I.

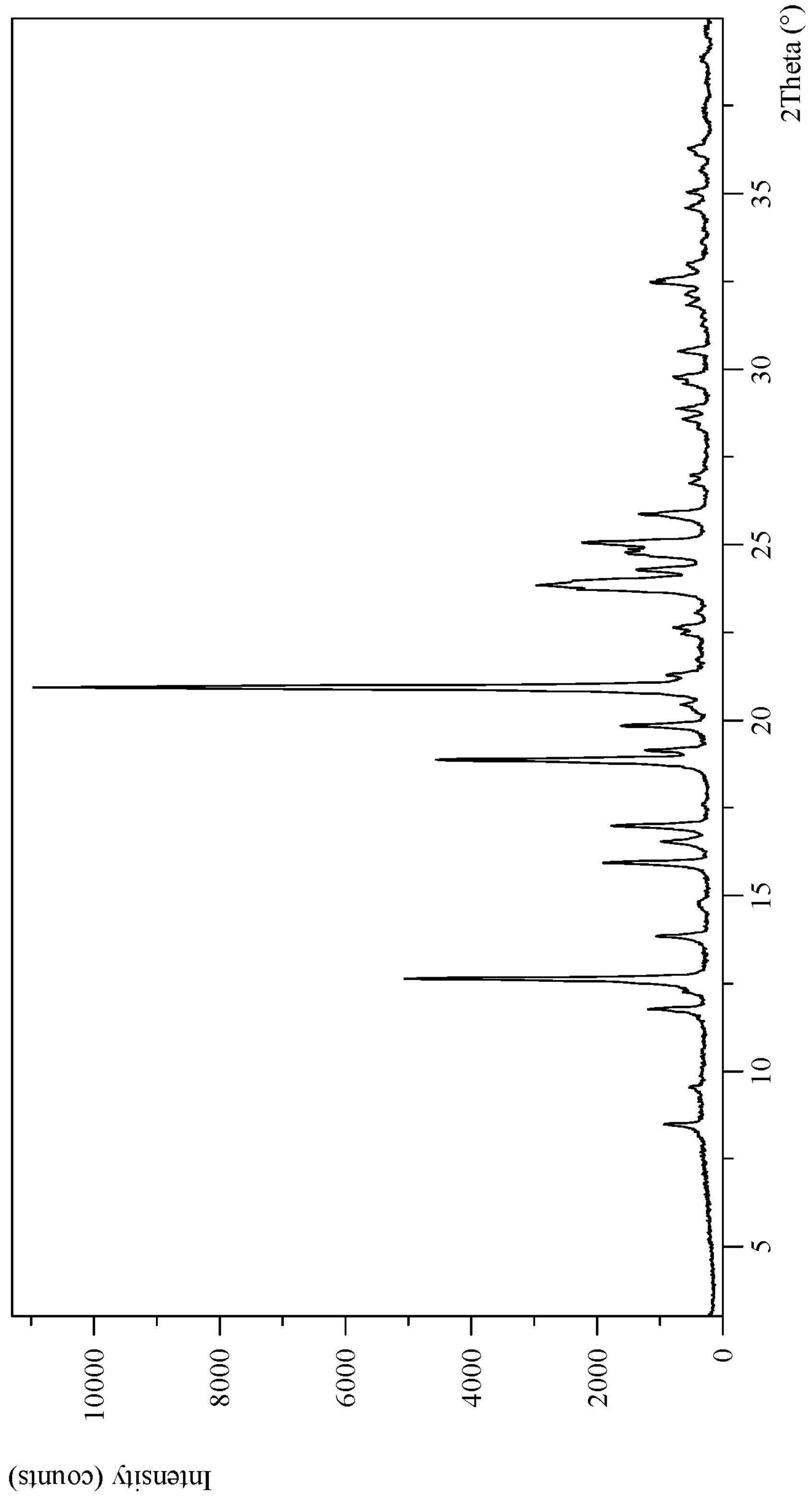
Figure 2. XRPD pattern of Asciminib hydrochloride, Form A.

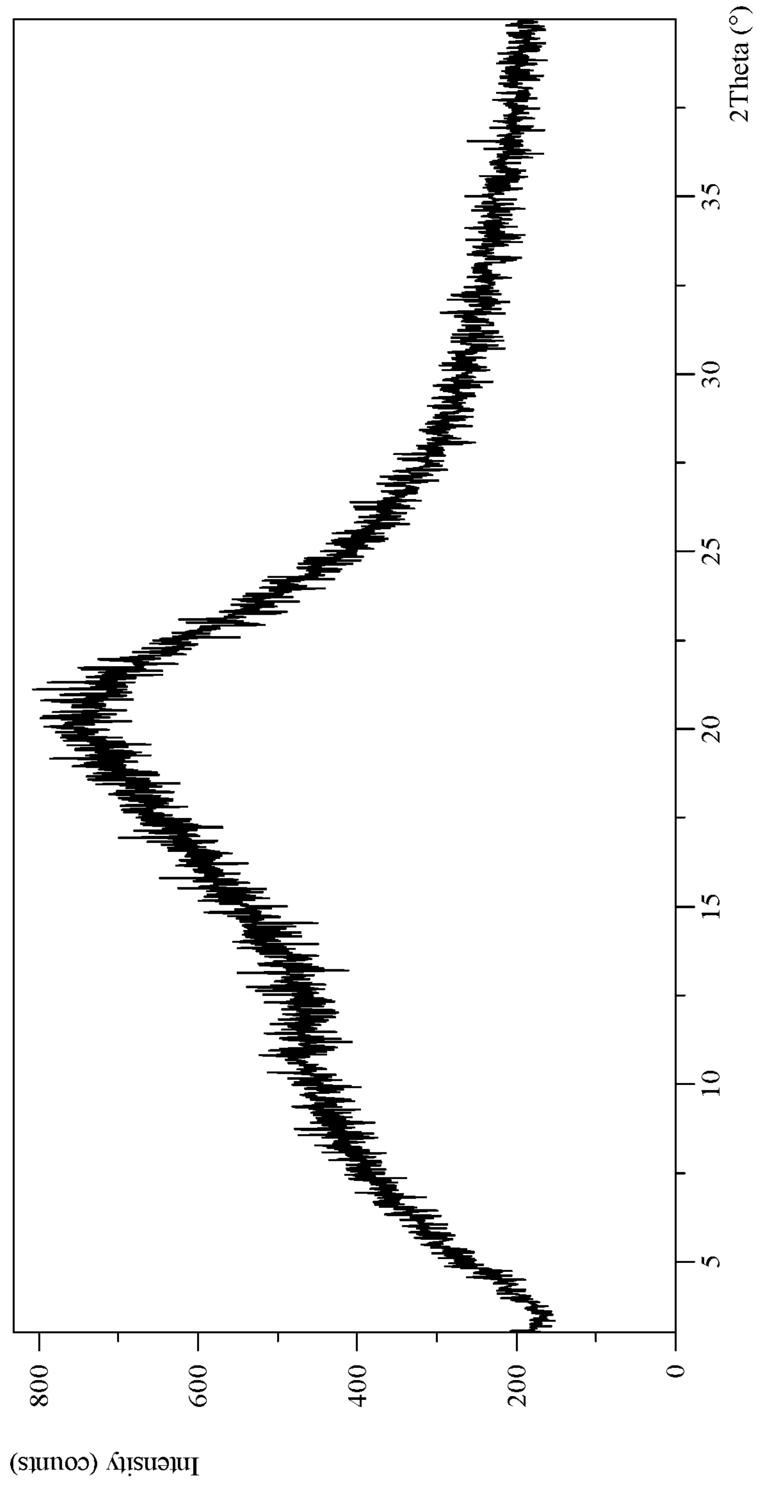
Figure 3. XRPD pattern of Asciminib amorphous form

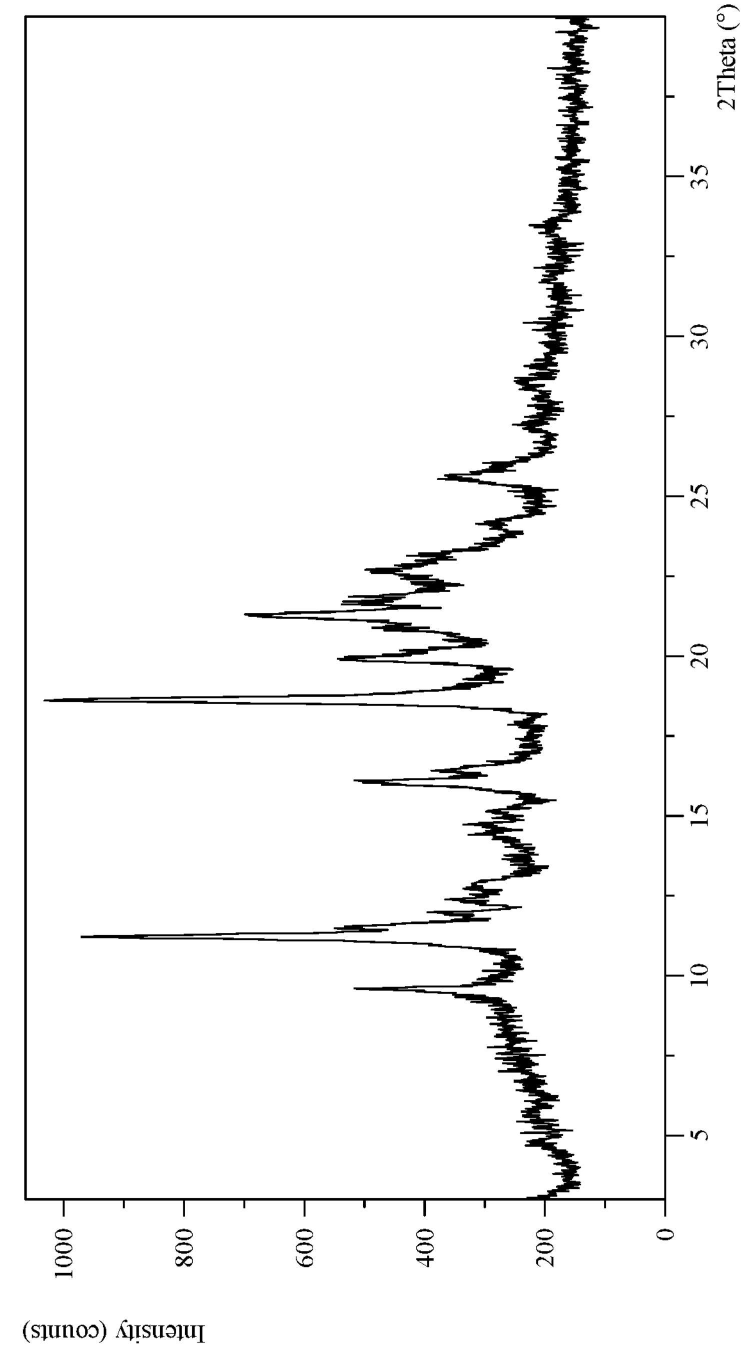
Figure 4. XRPD pattern of Asciminib, Form 2

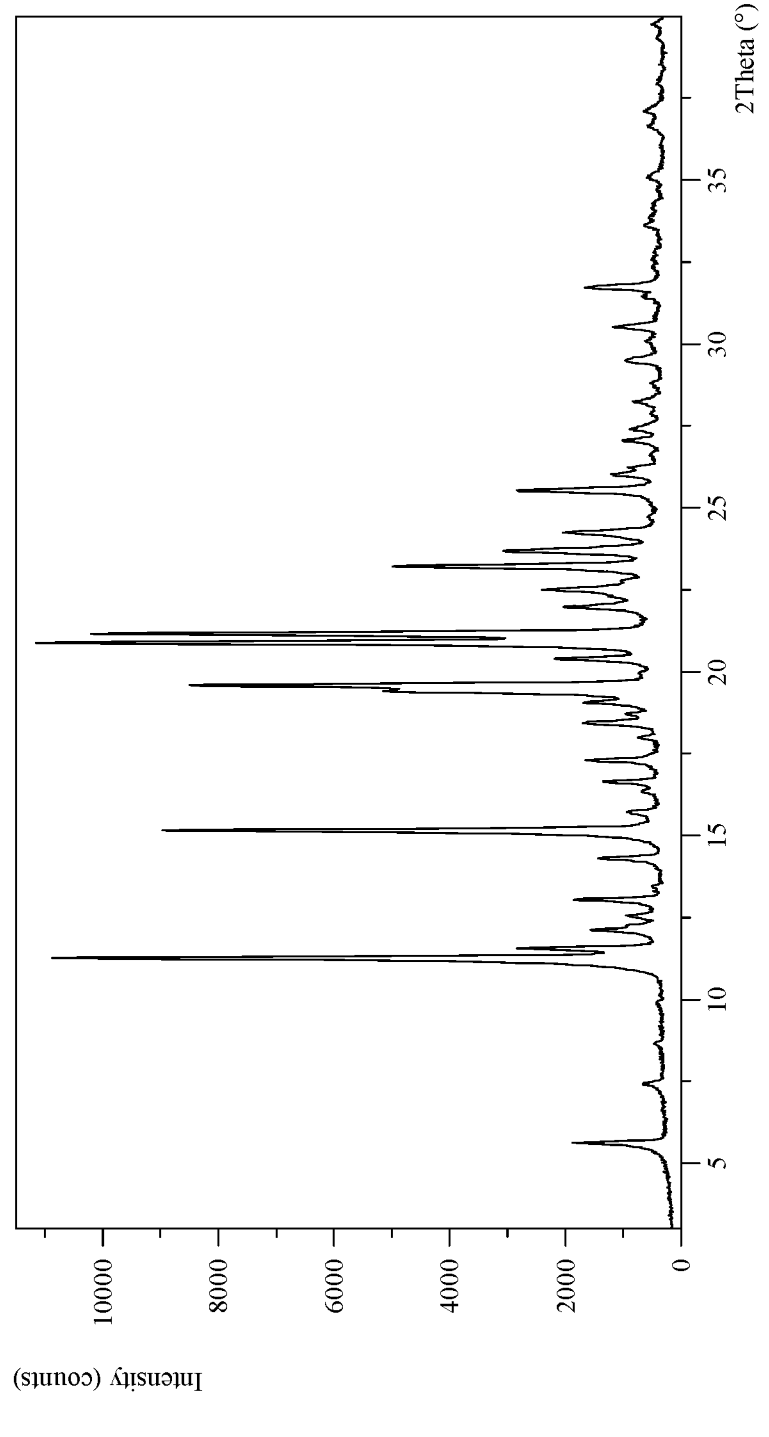
Figure 5. XRPD pattern of Asciminib, Form 3 (1-propanol solvate)

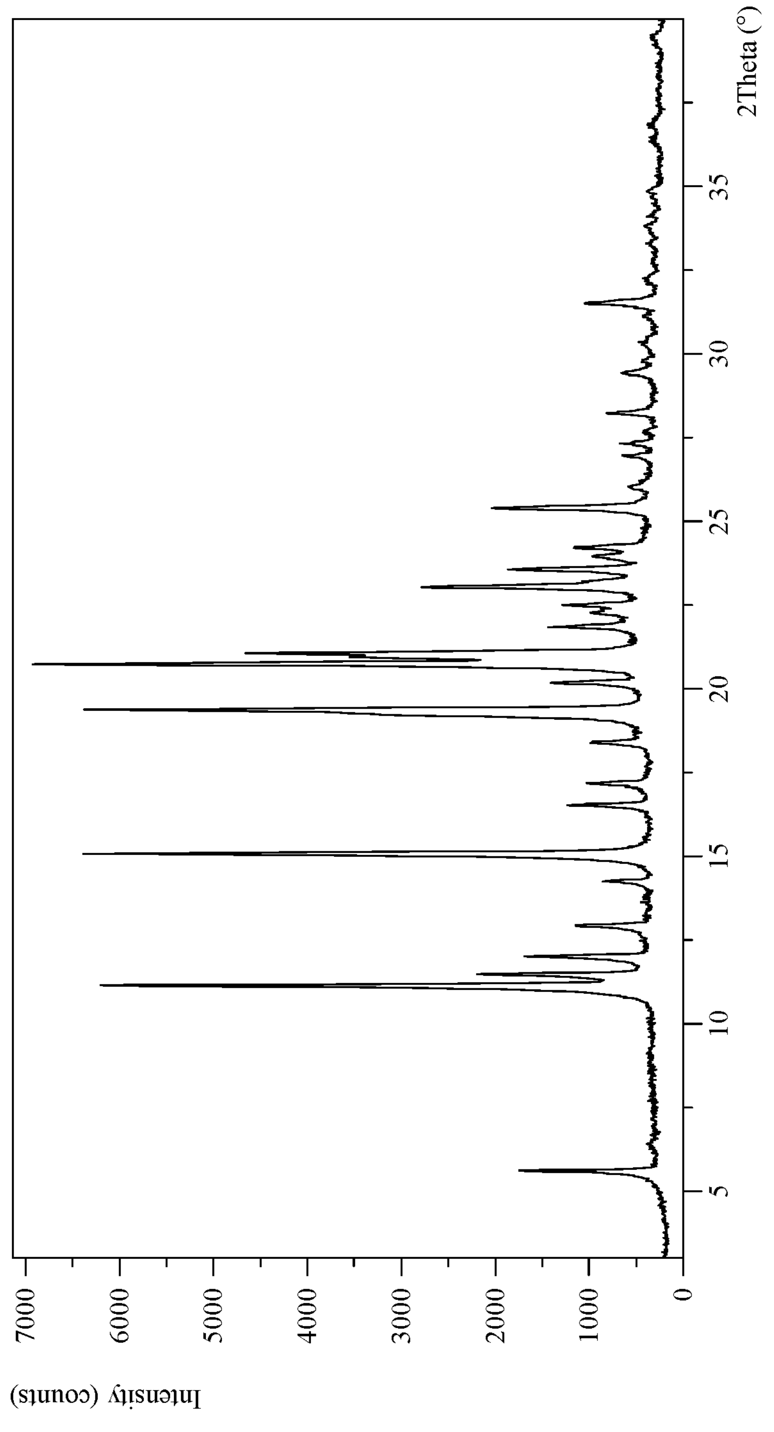
Figure 6. XRPD pattern of Asciminib, Form 3 (1-butanol solvate)

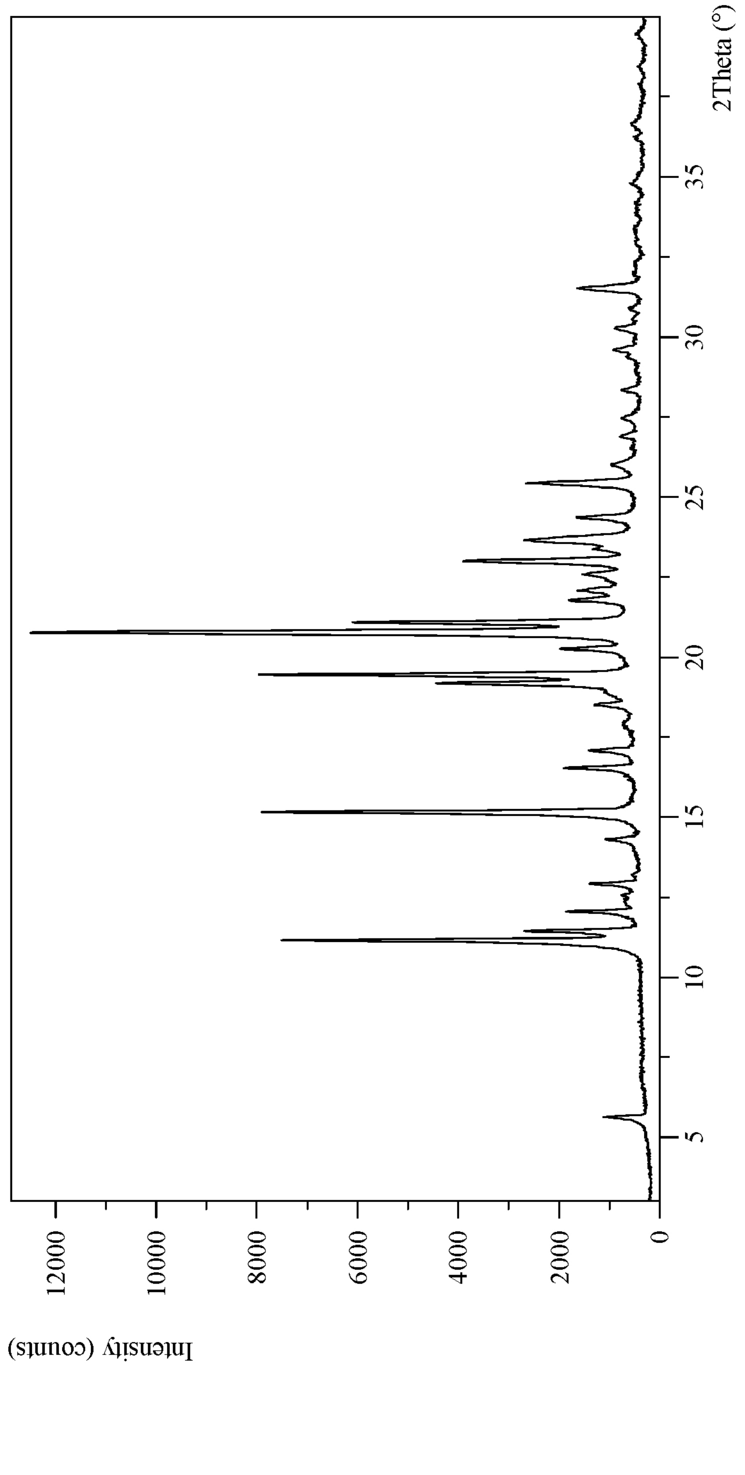
Figure 7 XRPD pattern of Asciminib, Form 3 (*i*-butanol solvate)

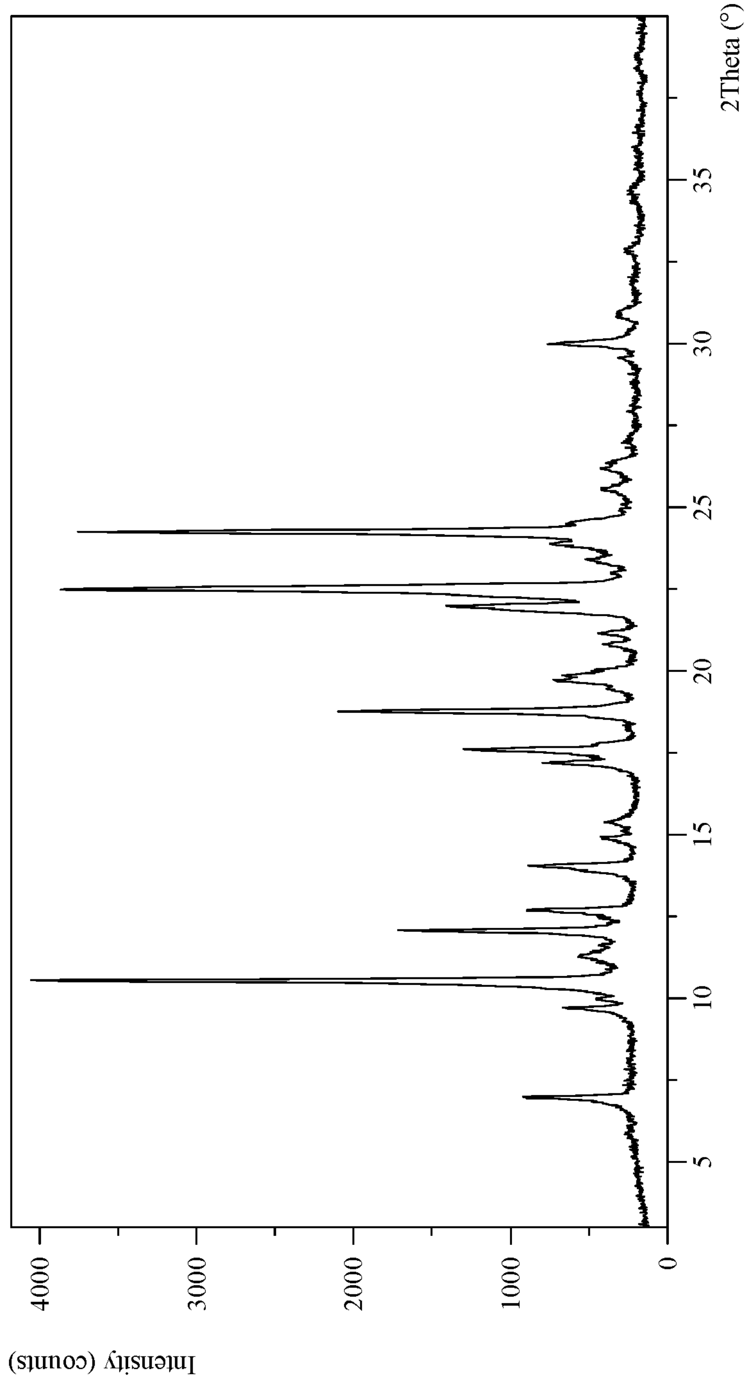
Figure 8. XRPD pattern of Asciminib, Form 4

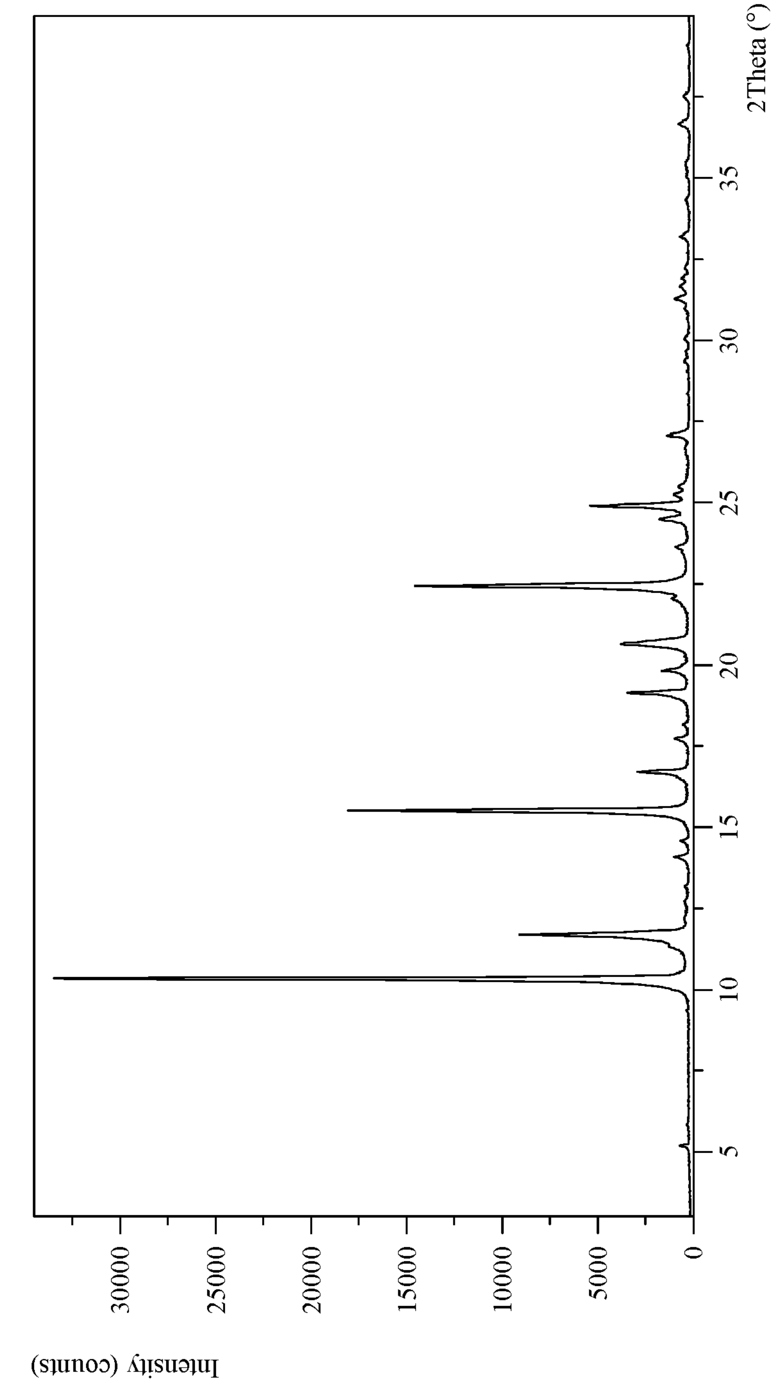
Figure 9. XRPD pattern of Asciminib, Form 5

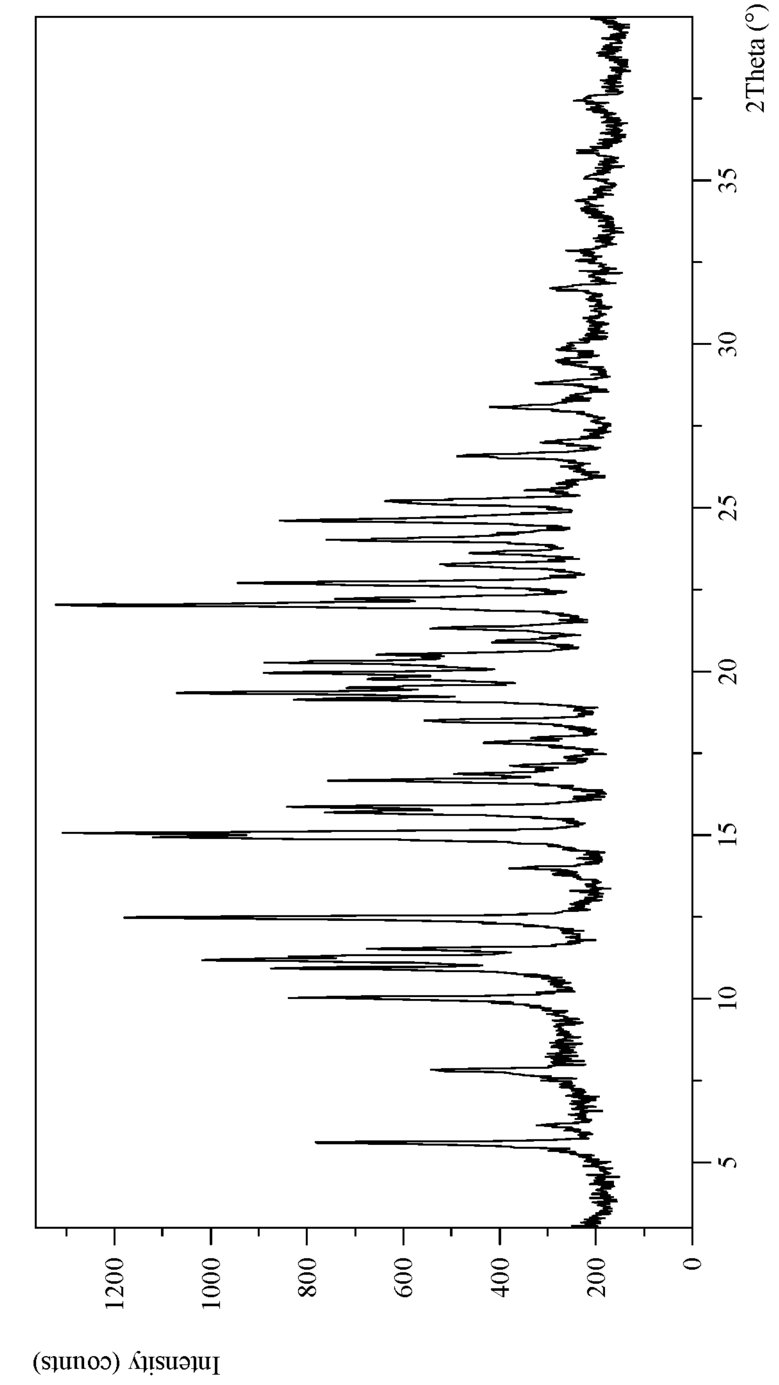
Figure 10. XRPD pattern of Asciminib, Form 6 (2-methyl-THF solvate)

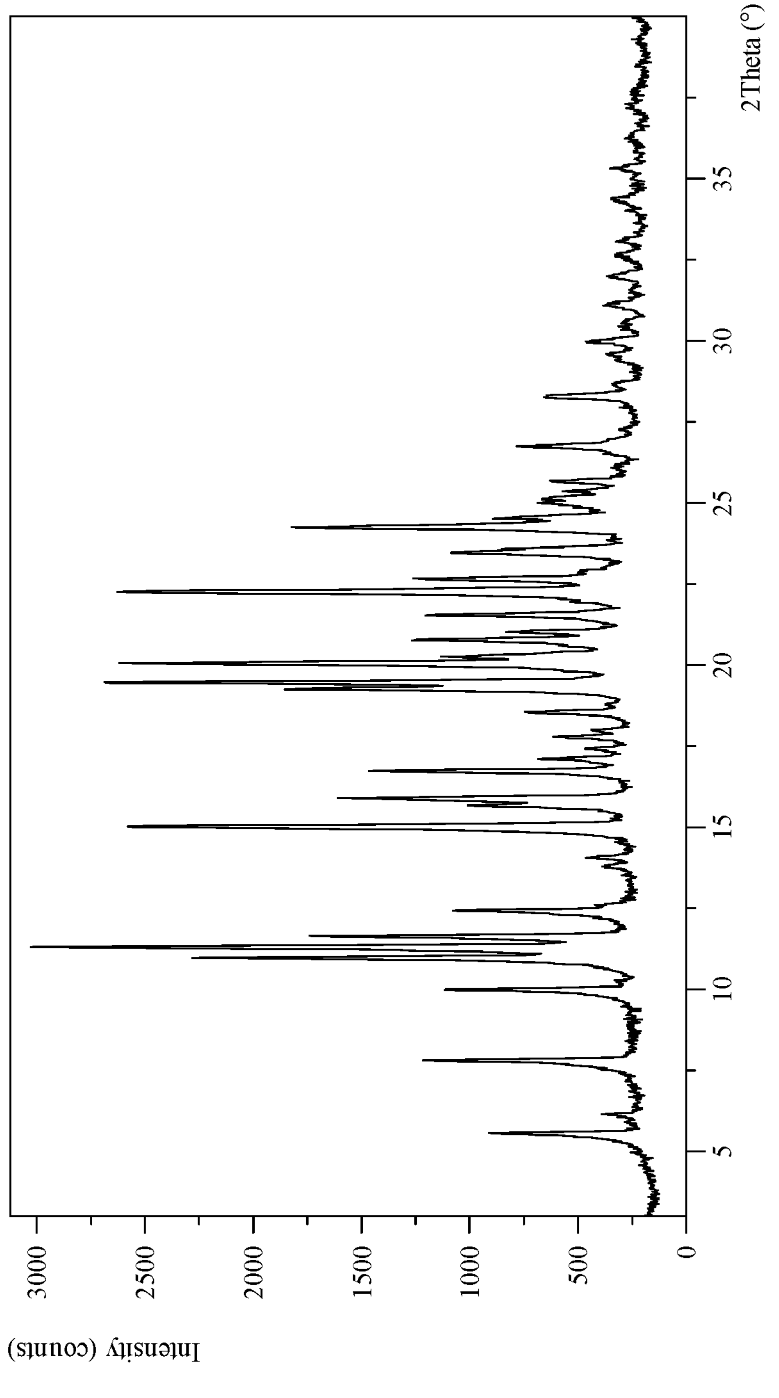
Figure 11. XRPD pattern of Asciminib, Form 6 (MEK solvate)

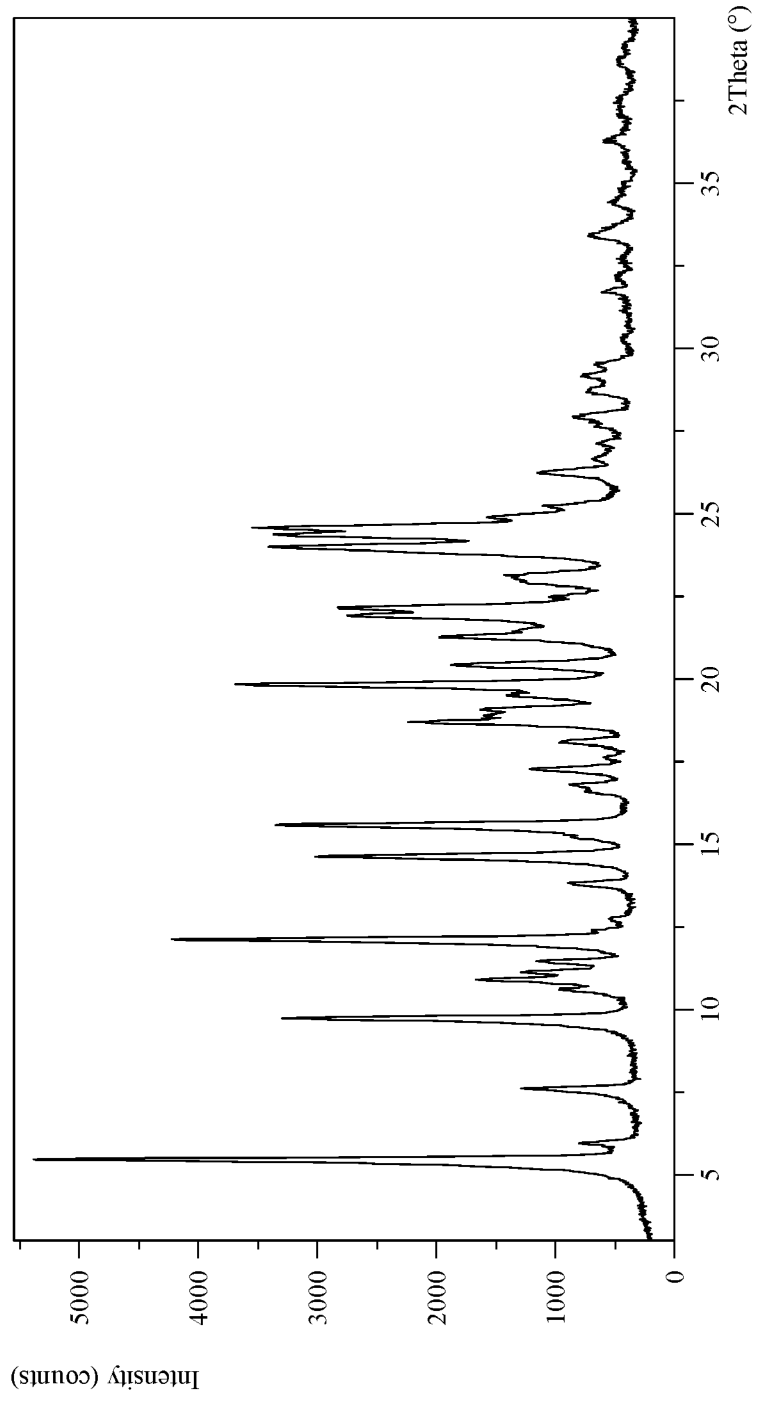
Figure 12. XRPD pattern of Asciminib, Form 7

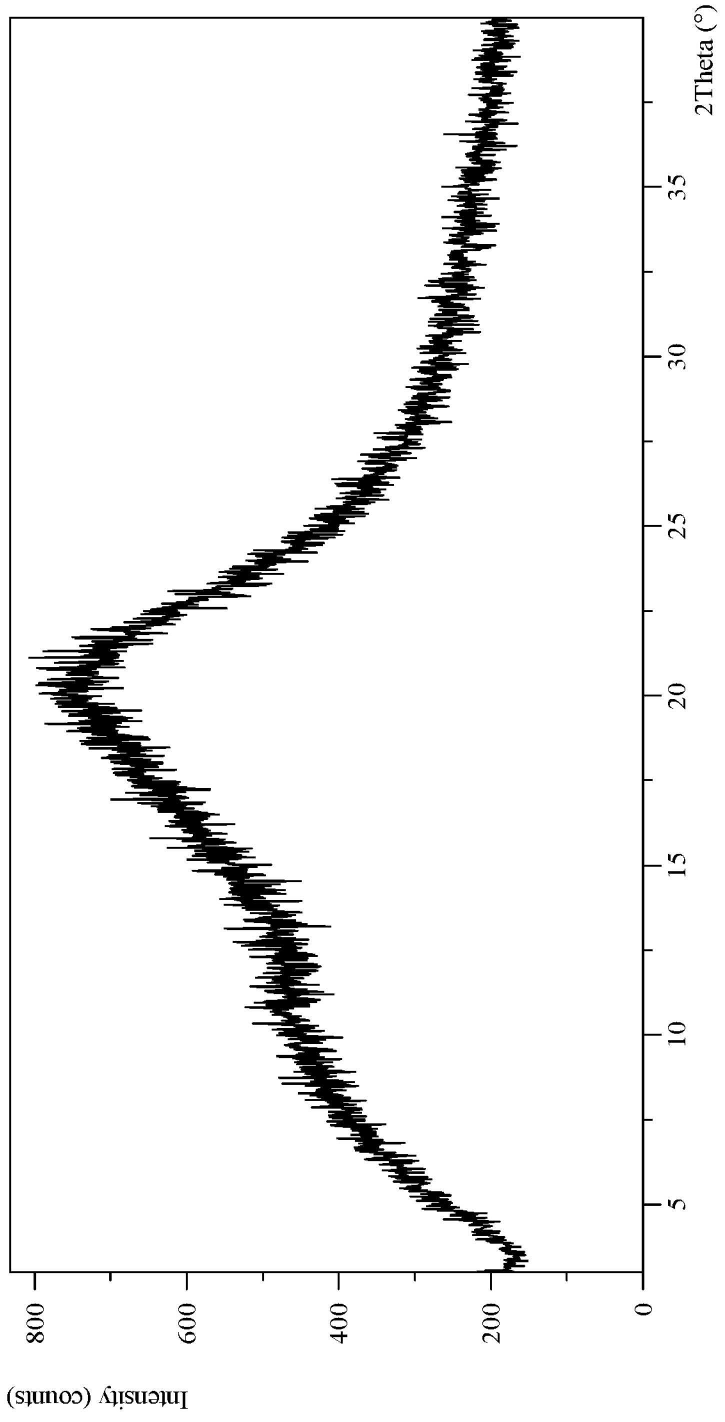
Figure 13. XRPD pattern of Asciminib HCl amorphous form

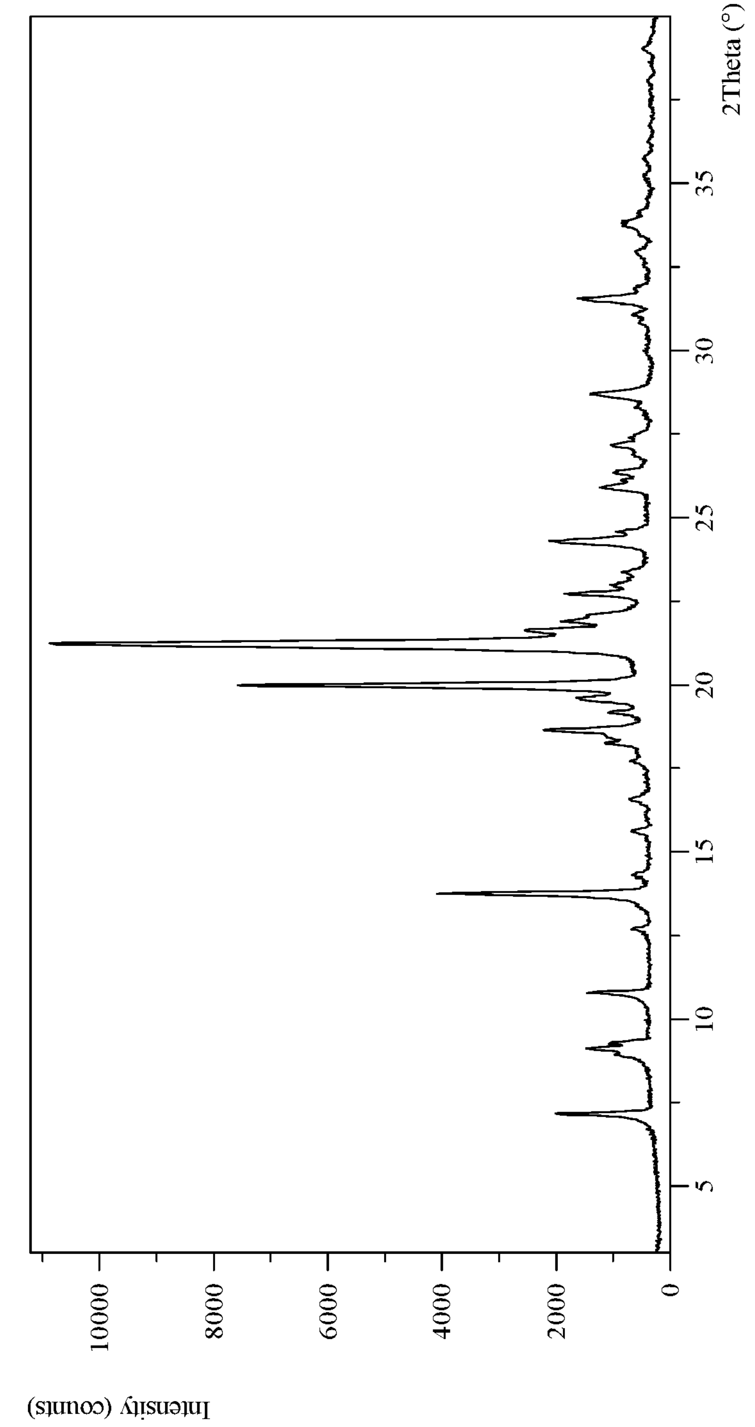
Figure 14. XRPD pattern of Asciminib HCl Form B

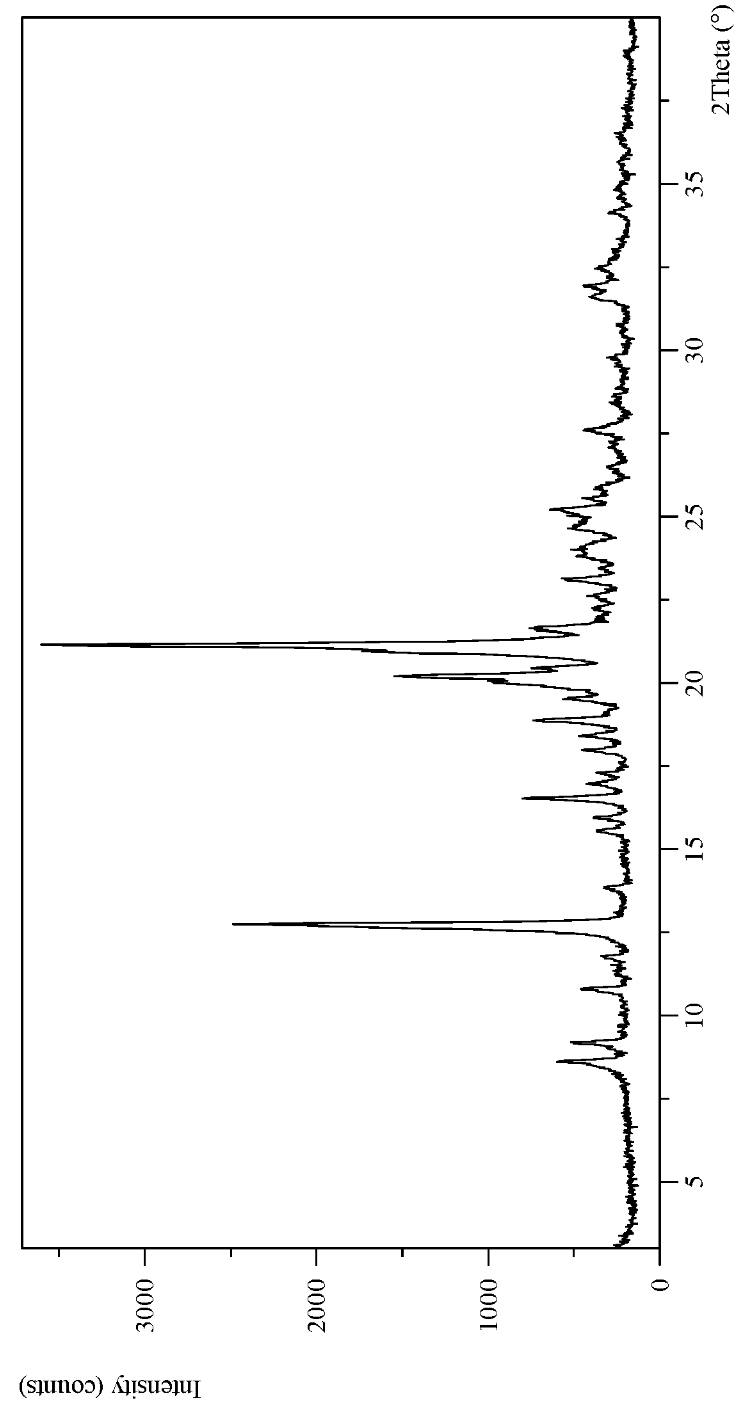
Figure 15. XRPD pattern of Asciminib HCl Form C in a mixture with Asciminib HCl Form A

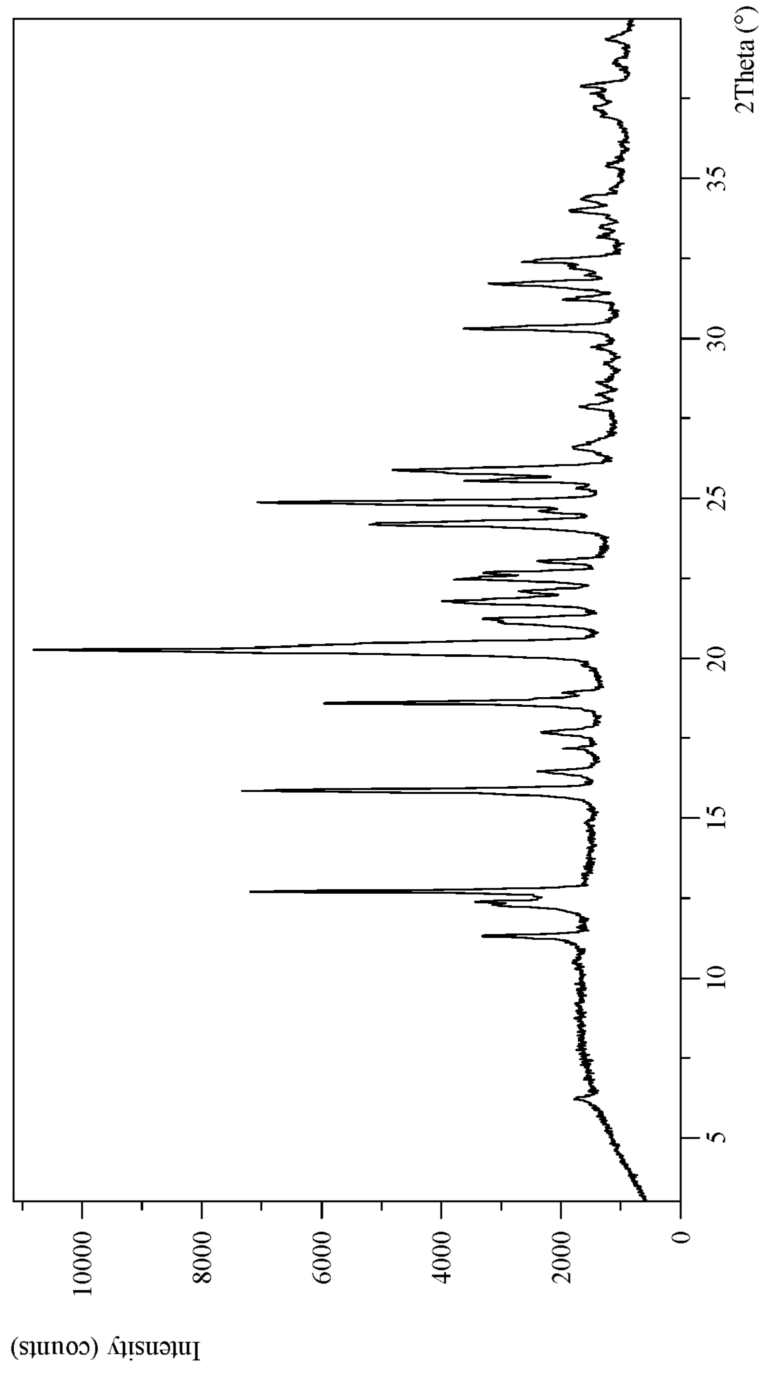
Figure 16. XRPD pattern of Asciminib HBr Form A

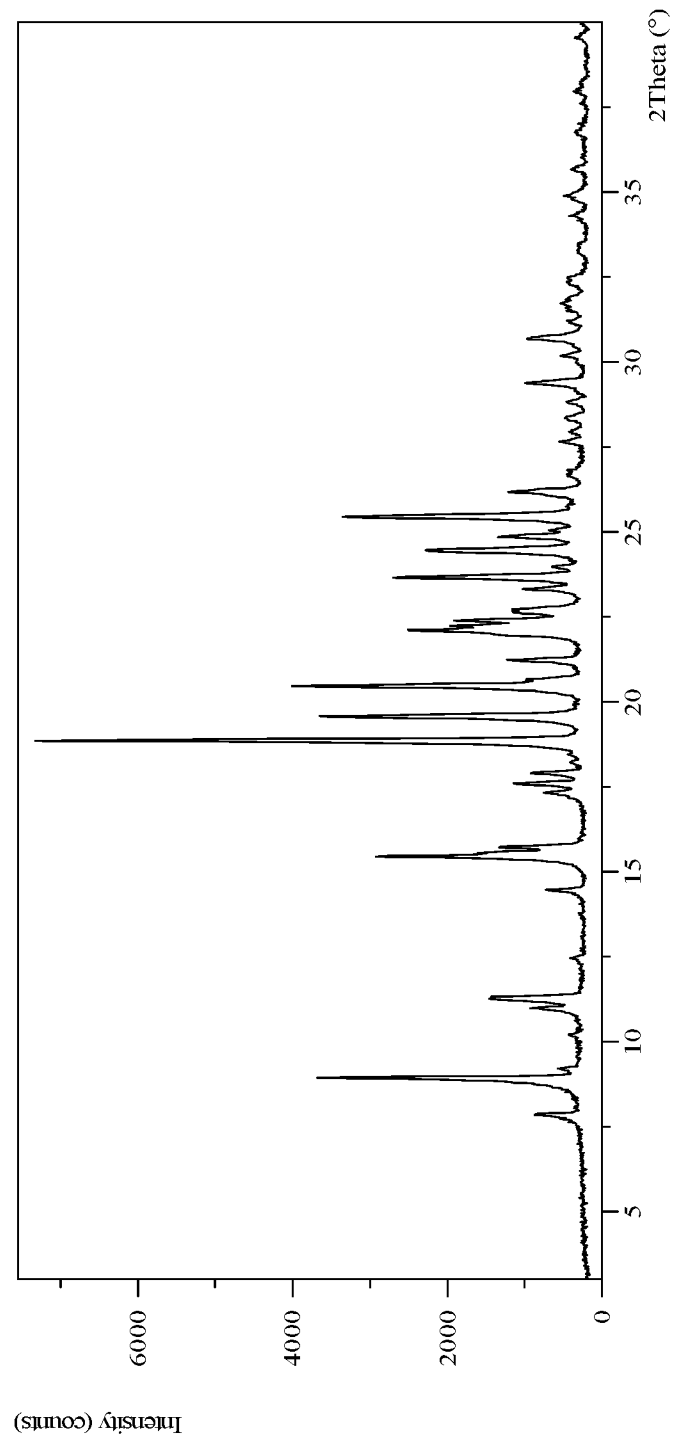
Figure 17. XRPD pattern of Asciminib mesylate Form A

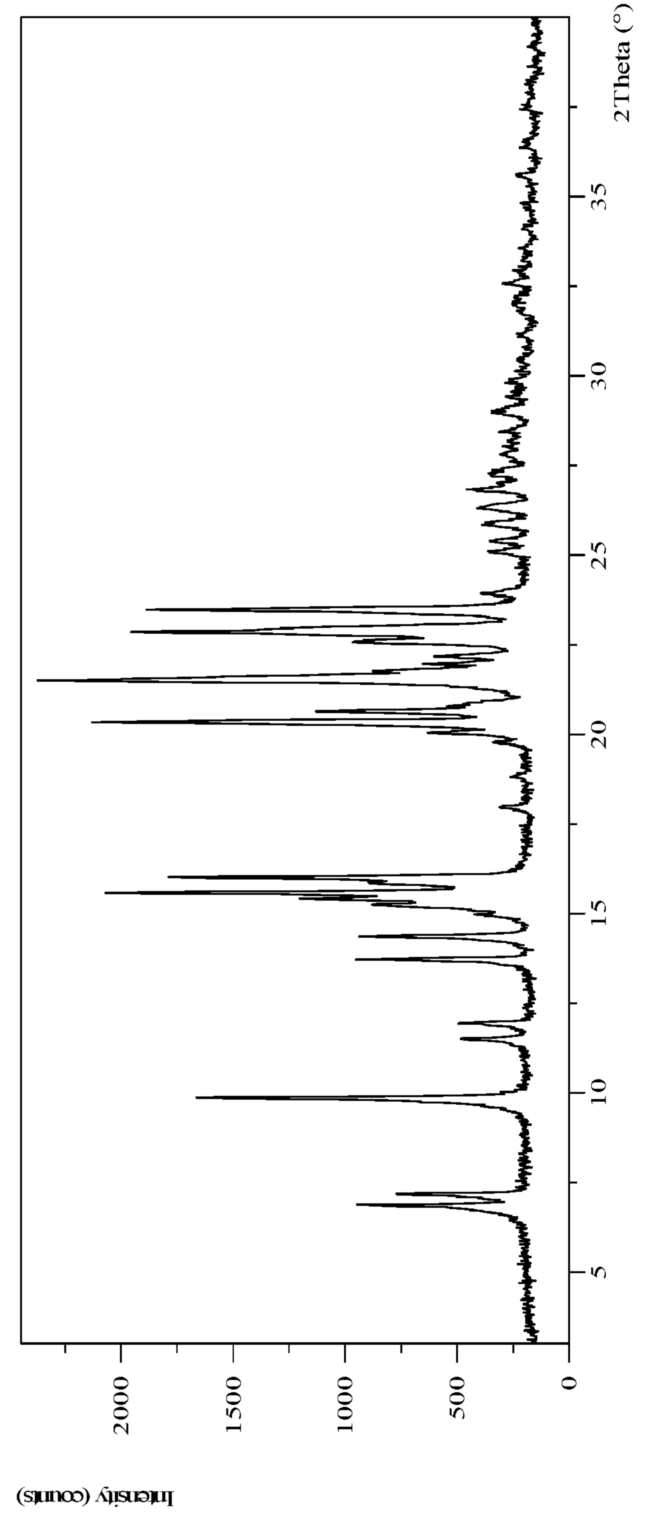
Figure 18. XRPD pattern of Asciminib phosphate Form A

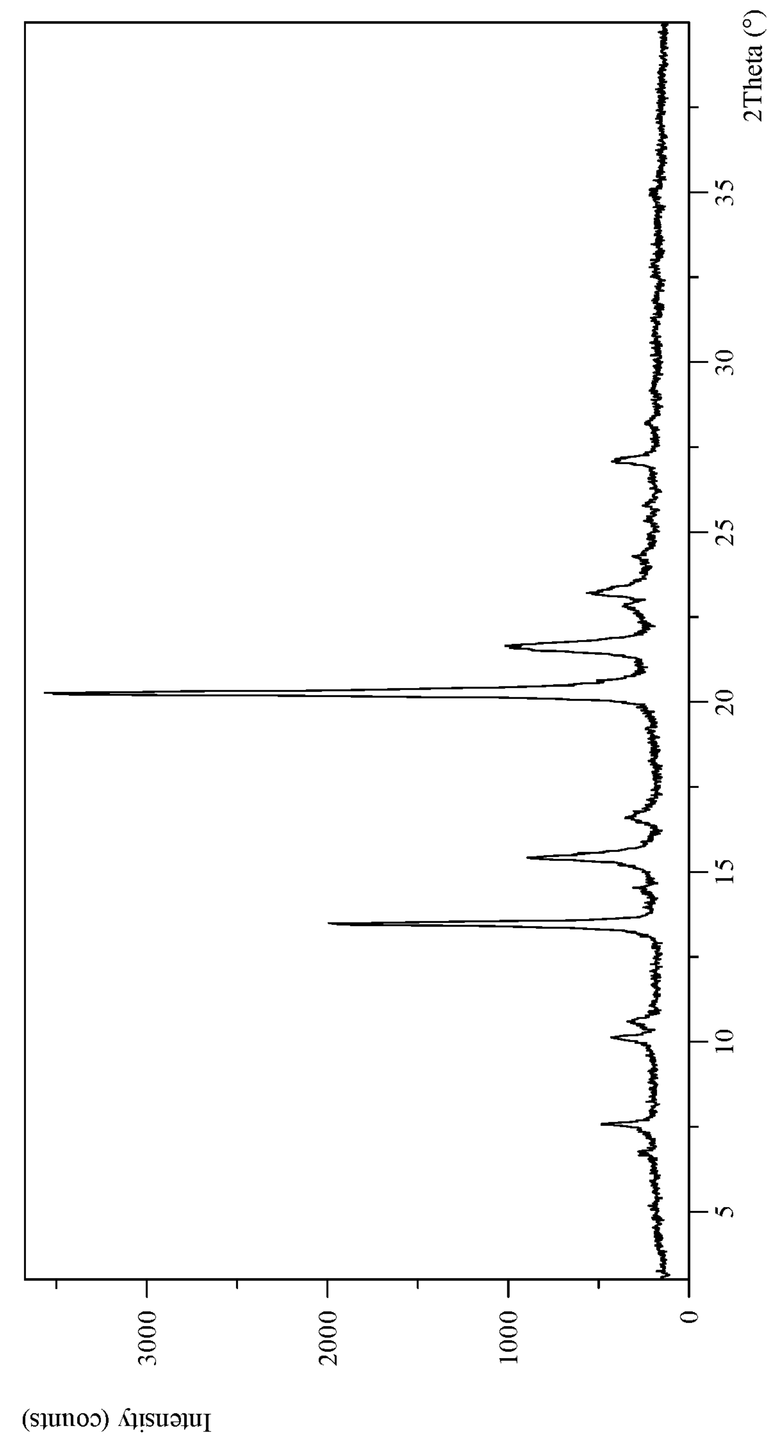
Figure 19. XRPD pattern of Asciminib sulphate Form A

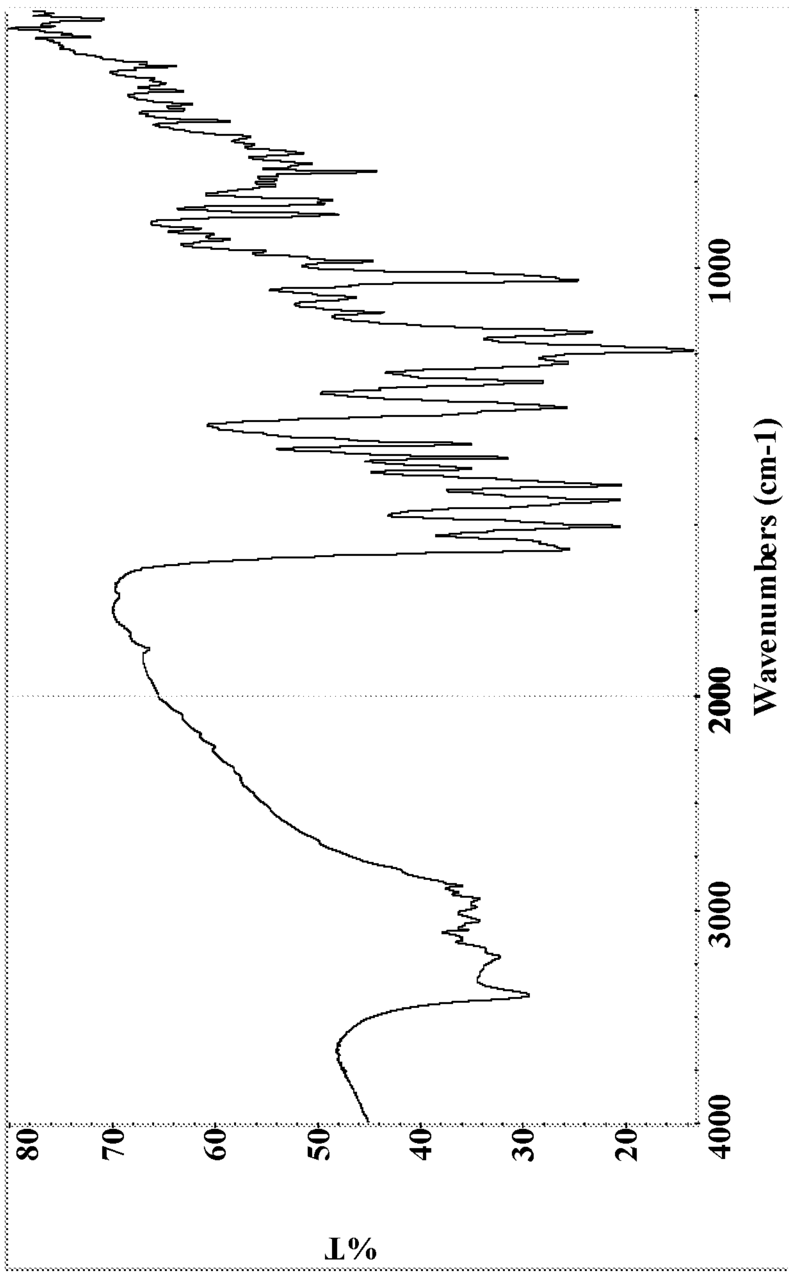
Figure 20. A characteristic FTIR spectrum of Asciminib hydrobromide Form A

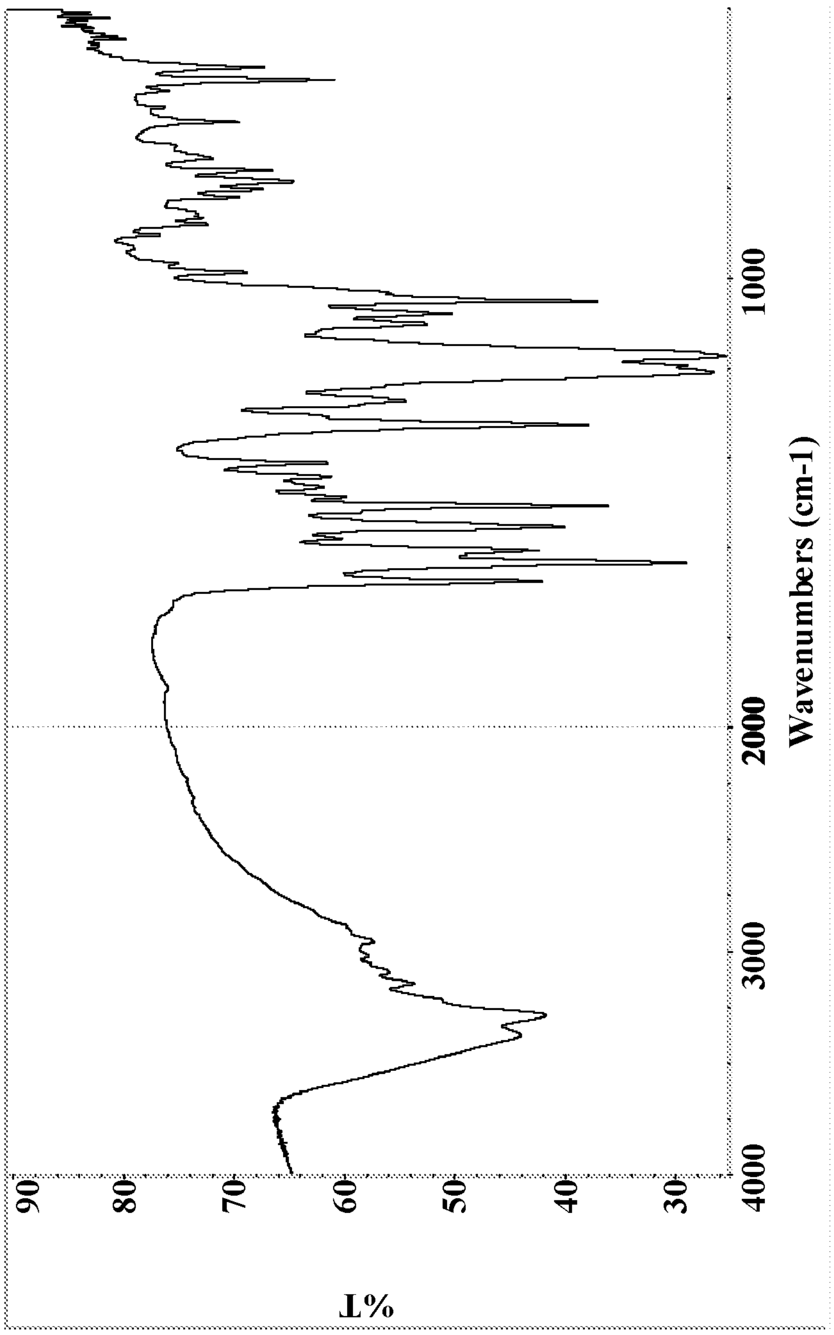
Figure 21. a characteristic FTIR spectrum of Asciminib mesylate Form A

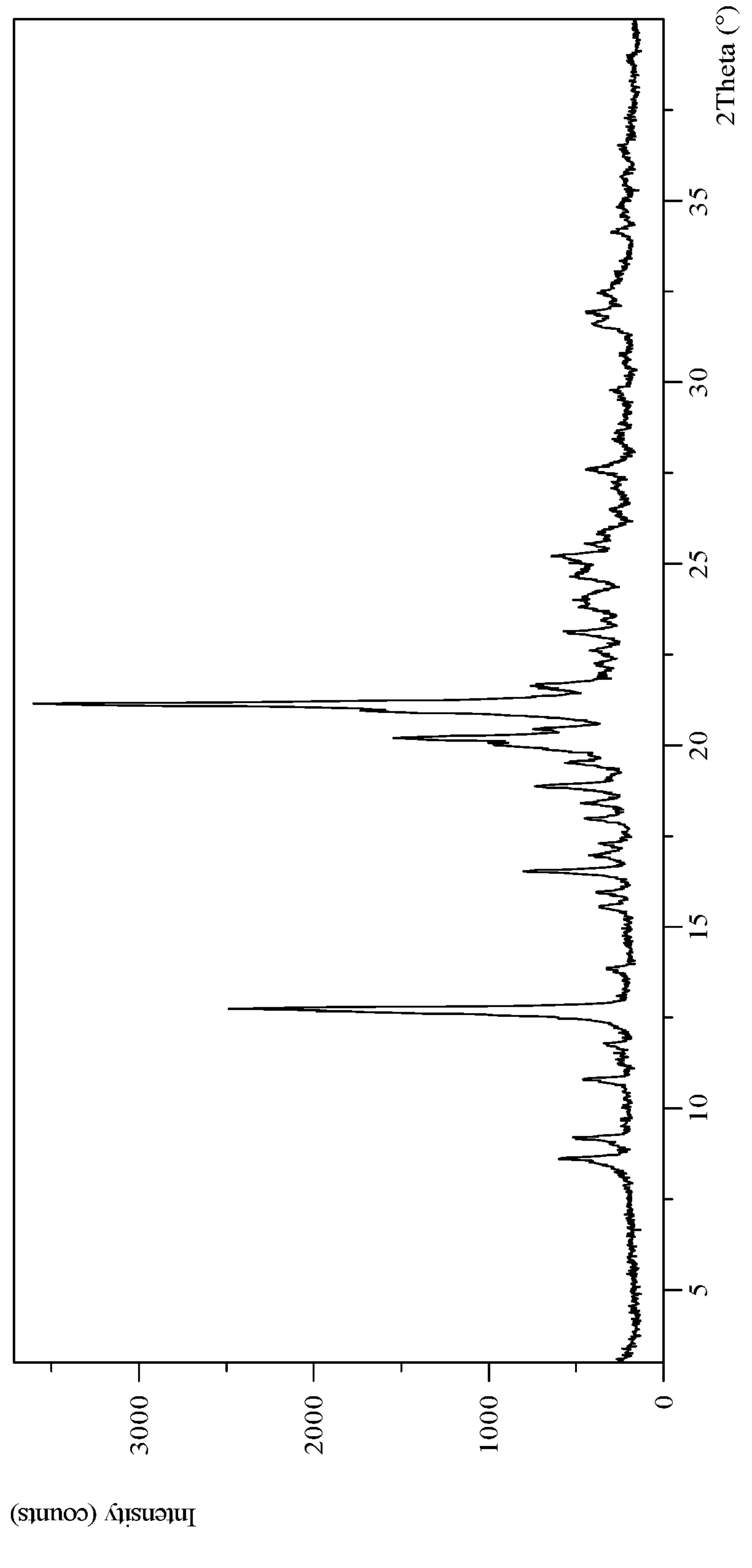
Figure 22. XRPD pattern of Asciminib HCl Form C

SOLID STATE FORMS OF ASCIMINIB AND PROCESSES FOR THE PREPARATION THEREOF

CROSS REFERENCE TO RELATED APPLICATIONS

This application is a National Stage of, and claims priority to and the benefit of, International Patent Application No. PCT/US2021/015468, filed Jan. 28, 2021, which, in turn, claims the benefit of and priority to, U.S. Provisional Application No. 62/966,625, filed Jan. 28, 2020; U.S. Provisional Application No. 63/005,539, filed Apr. 6, 2020; U.S. Provisional Application No. 63/035,933, filed Jun. 8, 2020; and U.S. Provisional Application No. 63/052,589, filed Jul. 16, 2020, the entire disclosures of each of which are incorporated by reference herein.

FIELD OF THE DISCLOSURE

The present disclosure encompasses solid state forms of Asciminib and salts thereof, in embodiments crystalline polymorphs of Asciminib and salts thereof, processes for preparation thereof, and pharmaceutical compositions thereof.

BACKGROUND OF THE DISCLOSURE

Asciminib, N-[4-[chloro(difluoro) methoxy]phenyl]-6-[(3R)-3-hydroxypyrrolidin-1-yl]-5-(1H-pyrazol-5-yl)pyridine-3-carboxamide, has the following chemical structure:

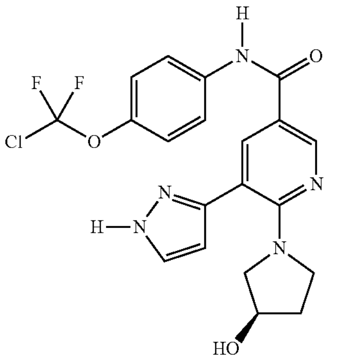 [SMILES: O=C(Nc1ccc(OC(F)(F)Cl)cc1)c1cnc(N2CC[C@@H](O)C2)c(-c2cc[nH]n2)c1]

Asciminib, also known as ABL001, is reported to be an investigational allosteric BCR-ABL inhibitor, and it is developed for the treatment of Chronic Myeloid Leukemia (CML) and Philadelphia chromosome-positive acute lymphoblastic leukemia.

The compound is described in U.S. Pat. No. 8,829,195.

Crystalline forms of Asciminib are described in International Publication No. WO2020/230099.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Asciminib.

SUMMARY OF THE DISCLOSURE

The present disclosure provides crystalline polymorphs of Asciminib and salts thereof, processes for preparation thereof, and pharmaceutical compositions thereof. These crystalline polymorphs can be used to prepare other solid state forms of Asciminib, Asciminib salts and their solid state forms.

The present disclosure also provides uses of the said solid state forms of Asciminib in the preparation of other solid state forms of Asciminib or salts thereof.

The present disclosure provides crystalline polymorphs of Asciminib for use in medicine, including for the treatment of Chronic Myeloid Leukemia (CML) and Philadelphia chromosome-positive acute lymphoblastic leukemia.

The present disclosure also encompasses the use of crystalline polymorphs of Asciminib of the present disclosure for the preparation of pharmaceutical compositions and/or formulations.

In another aspect, the present disclosure provides pharmaceutical compositions comprising crystalline polymorphs of Asciminib according to the present disclosure.

The present disclosure includes processes for preparing the above mentioned pharmaceutical compositions. The processes include combining any one or a combination of the crystalline polymorphs of Asciminib with at least one pharmaceutically acceptable excipient.

The crystalline polymorph of Asciminib as defined herein and the pharmaceutical compositions or formulations of the crystalline polymorph of Asciminib may be used as medicaments, such as for the treatment of Chronic Myeloid Leukemia (CML) and Philadelphia chromosome-positive acute lymphoblastic leukemia.

The present disclosure also provides methods of treating Chronic Myeloid Leukemia (CML) and Philadelphia chromosome-positive acute lymphoblastic leukemia, by administering a therapeutically effective amount of any one or a combination of the crystalline polymorphs of Asciminib of the present disclosure, or at least one of the above pharmaceutical compositions, to a subject suffering from Chronic Myeloid Leukemia (CML) and Philadelphia chromosome-positive acute lymphoblastic leukemia, or otherwise in need of the treatment.

The present disclosure also provides uses of crystalline polymorphs of Asciminib of the present disclosure, or at least one of the above pharmaceutical compositions, for the manufacture of medicaments for treating e.g., Chronic Myeloid Leukemia (CML) and Philadelphia chromosome-positive acute lymphoblastic leukemia.

BRIEF DESCRIPTION OF THE DRAWINGS

FIG. 1 shows a characteristic X-ray powder diffraction pattern (XRPD) of Asciminib Form 1.

FIG. 2 shows a characteristic XRPD of Asciminib hydrochloride Form A.

FIG. 3 shows a characteristic XRPD of Asciminib amorphous form.

FIG. 4 shows a characteristic XRPD of Asciminib Form 2.

FIG. 5 shows a characteristic XRPD of Asciminib Form 3 (1-propanol solvate).

FIG. 6 shows a characteristic XRPD of Asciminib Form 3 (1-butanol solvate).

FIG. 7 shows a characteristic XRPD of Asciminib Form 3 (i-butanol solvate).

FIG. 8 shows a characteristic XRPD of Asciminib Form 4.

FIG. 9 shows a characteristic XRPD of Asciminib Form 5.

FIG. 10 shows a characteristic XRPD of Asciminib Form 6 (2-methyl-THF solvate).

FIG. 11 shows a characteristic XRPD of Asciminib Form 6 (MEK solvate).

FIG. 12 shows a characteristic XRPD of Asciminib Form 7.

FIG. 13 shows a characteristic XRPD of Asciminib hydrochloride amorphous form.

FIG. 14 shows a characteristic XRPD of Asciminib hydrochloride Form B.

FIG. 15 shows a characteristic XRPD of Asciminib hydrochloride Form C in a mixture with form A.

FIG. 16 shows a characteristic XRPD of Asciminib hydrobromide Form A.

FIG. 17 shows a characteristic XRPD of Asciminib mesylate Form A.

FIG. 18 shows a characteristic XRPD of Asciminib phosphate Form A.

FIG. 19 shows a characteristic XRPD of Asciminib sulphate Form A.

FIG. 20 shows a characteristic FTIR spectrum of Asciminib hydrobromide Form A.

FIG. 21 shows a characteristic FTIR spectrum of Asciminib mesylate Form A.

FIG. 22 shows a characteristic XRPD spectrum of Asciminib mesylate Form C.

DETAILED DESCRIPTION OF THE DISCLOSURE

The present disclosure encompasses solid state forms of Asciminib and salts thereof, including crystalline polymorphs of Asciminib and salts thereof, processes for preparation thereof, and pharmaceutical compositions thereof.

Solid state properties of Asciminib and salts thereof and crystalline polymorphs thereof can be influenced by controlling the conditions under which Asciminib and salts thereof and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Asciminib and salts thereof described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Asciminib and salts thereof. In some embodiments of the disclosure, the described crystalline polymorph of Asciminib and salts thereof may contain from about 1% to about 20% (w/w), from about 5% to about 20% (w/w), or from about 5% to about 10% (w/w) of one or more other crystalline polymorph of the same Asciminib.

Depending on which other crystalline polymorphs a comparison is made, the crystalline polymorphs of Asciminib and salts thereof of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal in form of Asciminib and salts thereof referred to herein as being characterized by graphical data "as depicted in" or "as substantially depicted in" a Figure will thus be understood to include any crystal forms of Asciminib and salts thereof characterized with the graphical data having such small variations, as are well known to the skilled person, in comparison with the Figure.

As used herein, and unless stated otherwise, the term "anhydrous" in relation to crystalline forms of Asciminib and salts thereof, relates to a crystalline form of Asciminib which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of Asciminib and salts thereof of the present disclosure corresponds to a crystalline polymorph of Asciminib and salts thereof that is physically separated from the reaction mixture in which it is formed.

As used herein, unless stated otherwise, the XRPD measurements are taken using copper Kα radiation wavelength 1.54187 Å. XRPD peaks reported herein are measured using CuK α radiation, λ=1.54187 Å, typically at a temperature of 25±3° C.

As used herein, unless stated otherwise, FTIR measurements are taken using KBr pellet, As used herein, unless stated otherwise, $^{13}C$ NMR reported herein are measured at 125 MHz at a magic angle spinning frequency $\omega_r/2\pi$=11 kHz, preferably at a temperature of at 293 K±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Asciminib, designated Form 1. The crystalline Form 1 of Asciminib may be characterized by data selected from one or more of the following: an X-ray powder diffraction pattern substantially as depicted in FIG. 1; an X-ray powder diffraction pattern having peaks at 11.3, 15.4, 19.0, 22.2 and 23.4 degrees 2-theta±0.2 degrees 2-theta; and combinations of these data.

Crystalline Form 1 of Asciminib may be further characterized by an X-ray powder diffraction pattern having peaks at 11.3, 15.4, 19.0, 22.2 and 23.4 degrees 2-theta±0.2 degrees 2-theta, and also having any one, two, three, four or five additional peaks selected from 5.8, 12.7, 19.9, 21.9 and 25.5 degrees 2-theta±0.2 degrees 2-theta.

Crystalline Form 1 of Asciminib may be alternatively characterized by an X-ray powder diffraction pattern having peaks at 5.8, 11.3, 12.7, 15.4, 19.0, 19.9, 21.9, 22.2, 23.4, and 25.5 degrees 2-theta±0.2 degrees 2-theta, and also having any one, two, three, four or five additional peaks selected from degrees 2-theta±0.2 degrees 2-theta.

In one embodiment of the present disclosure, crystalline Form 1 of Asciminib is isolated.

Crystalline Form 1 of Asciminib may be anhydrous form.

Crystalline Form 1 of Asciminib may be characterized by each of the above characteristics alone/or by all possible combinations, e.g., an XRPD pattern having peaks at 11.3, 15.4, 19.0, 22.2 and 23.4 degrees 2-theta±0.2 degrees 2-theta; an XRPD pattern as depicted in FIG. 1, and combinations thereof.

The present disclosure includes an amorphous form of Asciminib. The amorphous form of Asciminib may be characterized by an X-ray powder diffraction pattern substantially as depicted in FIG. 3.

The present disclosure includes a crystalline polymorph of Asciminib, designated Form 2. The crystalline Form 2 of Asciminib may be characterized by data selected from one or more of the following: an X-ray powder diffraction pattern substantially as depicted in FIG. 4; an X-ray powder diffraction pattern having peaks at 9.6, 11.2, 16.1 and 18.6 degrees 2-theta±0.2 degrees 2-theta; and combinations of these data.

Crystalline Form 2 of Asciminib may be further characterized by an X-ray powder diffraction pattern having peaks at 9.6, 11.2, 16.1 and 18.6 degrees 2-theta±0.2 degrees 2-theta, and also having any one, two or three additional peaks selected from 19.9, 21.3 and 25.6 degrees 2-theta±0.2 degrees 2-theta.

Crystalline Form 2 of Asciminib may be alternatively characterized by an X-ray powder diffraction pattern having peaks at 9.6, 11.2, 16.1, 18.6, 19.9, 21.3 and 25.6 degrees 2-theta±0.2 degrees 2-theta.

In one embodiment of the present disclosure, crystalline Form 2 of Asciminib is isolated.

Crystalline Form 2 of Asciminib may be 1,4-dioxane solvate.

Crystalline Form 2 of Asciminib may be characterized by each of the above characteristics alone/or by all possible combinations, e.g., an XRPD pattern having peaks at 9.6, 11.2, 16.1 and 18.6 degrees 2-theta±0.2 degrees 2-theta; an XRPD pattern as depicted in FIG. 4, and combinations thereof.

The present disclosure includes a crystalline polymorph of Asciminib, designated Form 3. The crystalline Form 3 of Asciminib may be characterized by data selected from one or more of the following: an X-ray powder diffraction pattern substantially as depicted in FIG. 5, 6 or 7; an X-ray powder diffraction pattern having peaks at 13.1, 17.3, 20.9 and 31.7 degrees 2-theta±0.2 degrees 2-theta; and combinations of these data.

Crystalline Form 3 of Asciminib may be further characterized by an X-ray powder diffraction pattern having peaks at 13.1, 17.3, 20.9 and 31.7 degrees 2-theta±0.2 degrees 2-theta, and also having any one, two, three or four additional peaks selected from 14.3, 20.4, 23.7 and 24.2 degrees 2-theta±0.2 degrees 2-theta.

Crystalline Form 3 of Asciminib may be alternatively characterized by an X-ray powder diffraction pattern having peaks at 13.1, 14.3, 17.3, 20.4, 20.9, 23.7, 24.2 and 31.7 degrees 2-theta±0.2 degrees 2-theta.

Crystalline Form 3 of Asciminib may be a solvate selected from 1-propanol, 1-butanol and isobutanol (i-butanol) solvates.

Form 3 (1-propanol solvate) of Asciminib may be characterized by data selected from one or more of the following: an X-ray powder diffraction pattern substantially as depicted in FIG. 5; an X-ray powder diffraction pattern having peaks at 13.1, 17.3, 20.9 and 31.7 degrees 2-theta±0.2 degrees 2-theta; and combinations of these data.

Crystalline Form 3 (1-propanol solvate) of Asciminib may be further characterized by an X-ray powder diffraction pattern having peaks at 13.1, 17.3, 20.9 and 31.7 degrees 2-theta±0.2 degrees 2-theta, and also having any one, two, three or four additional peaks selected from 14.3, 20.4, 23.7 and 24.2 degrees 2-theta±0.2 degrees 2-theta.

Crystalline Form 3 (1-propanol solvate) of Asciminib may be alternatively characterized by an X-ray powder diffraction pattern having peaks at 13.1, 14.3, 17.3, 20.4, 20.9, 23.7, 24.2 and 31.7 degrees 2-theta±0.2 degrees 2-theta.

Form 3 (1-butanol solvate) of Asciminib may be characterized by data selected from one or more of the following: an X-ray powder diffraction pattern substantially as depicted in FIG. 6; an X-ray powder diffraction pattern having peaks at 13.1, 17.3, 20.9 and 31.7 degrees 2-theta±0.2 degrees 2-theta; and combinations of these data.

Crystalline Form 3 (1-butanol solvate) of Asciminib may be further characterized by an X-ray powder diffraction pattern having peaks at 13.1, 17.3, 20.9 and 31.7 degrees 2-theta±0.2 degrees 2-theta, and also having any one, two, three or four additional peaks selected from 14.3, 20.4, 23.7 and 24.2 degrees 2-theta±0.2 degrees 2-theta.

Crystalline Form 3 (1-butanol solvate) of Asciminib may be alternatively characterized by an X-ray powder diffraction pattern having peaks at 13.1, 14.3, 17.3, 20.4, 20.9, 23.7, 24.2 and 31.7 degrees 2-theta±0.2 degrees 2-theta.

Form 3 (i-butanol solvate) of Asciminib may be characterized by data selected from one or more of the following: an X-ray powder diffraction pattern substantially as depicted in FIG. 7; an X-ray powder diffraction pattern having peaks at 13.1, 17.3, 20.9 and 31.7 degrees 2-theta±0.2 degrees 2-theta; and combinations of these data.

Crystalline Form 3 (i-butanol solvate) of Asciminib may be further characterized by an X-ray powder diffraction pattern having peaks at 13.1, 17.3, 20.9 and 31.7 degrees 2-theta±0.2 degrees 2-theta, and also having any one, two, three or four additional peaks selected from 14.3, 20.4, 23.7 and 24.2 degrees 2-theta±0.2 degrees 2-theta.

Crystalline Form 3 (i-butanol solvate) of Asciminib may be alternatively characterized by an X-ray powder diffraction pattern having peaks at 13.1, 14.3, 17.3, 20.4, 20.9, 23.7, 24.2 and 31.7 degrees 2-theta±0.2 degrees 2-theta.

In one embodiment of the present disclosure, crystalline Form 3 of Asciminib is isolated.

Crystalline Form 3 of Asciminib may be characterized by each of the above characteristics alone/or by all possible combinations, e.g., an XRPD pattern having peaks at 13.1, 17.3, 20.9 and 31.7 degrees 2-theta±0.2 degrees 2-theta; an XRPD pattern as depicted in FIG. 5, 6 or 7 and combinations thereof.

The present disclosure includes a crystalline polymorph of Asciminib, designated Form 4. The crystalline Form 4 of Asciminib may be characterized by data selected from one or more of the following: an X-ray powder diffraction pattern substantially as depicted in FIG. 8; an X-ray powder diffraction pattern having peaks at 7.0, 12.1, 14.0 and 22.5 degrees 2-theta±0.2 degrees 2-theta; and combinations of these data.

Crystalline Form 4 of Asciminib may be further characterized by an X-ray powder diffraction pattern having peaks at 7.0, 12.1, 14.0 and 22.5 degrees 2-theta±0.2 degrees 2-theta, and also having any one, two, three or four additional peaks selected from 10.0, 12.7, 17.6 and 30.0 degrees 2-theta±0.2 degrees 2-theta.

Crystalline Form 4 of Asciminib may be alternatively characterized by an X-ray powder diffraction pattern having peaks at 7.0, 10.0, 12.1, 12.7, 14.0, 17.6, 22.5, and 30.0 degrees 2-theta±0.2 degrees 2-theta.

In one embodiment of the present disclosure, crystalline Form 4 of Asciminib is isolated.

Crystalline Form 4 of Asciminib may be MeOH solvate.

Crystalline Form 4 of Asciminib may be characterized by each of the above characteristics alone/or by all possible combinations, e.g., an XRPD pattern having peaks at 7.0, 12.1, 14.0 and 22.5 degrees 2-theta±0.2 degrees 2-theta; an XRPD pattern as depicted in FIG. 8, and combinations thereof.

The present disclosure includes a crystalline polymorph of Asciminib, designated Form 5. The crystalline Form 5 of Asciminib may be characterized by data selected from one or more of the following: an X-ray powder diffraction pattern substantially as depicted in FIG. 9; an X-ray powder diffraction pattern having peaks at 10.3, 16.7, 20.6 and 24.9 degrees 2-theta±0.2 degrees 2-theta; and combinations of these data.

Crystalline Form 5 of Asciminib may be further characterized by an X-ray powder diffraction pattern having peaks at 10.3, 16.7, 20.6 and 24.9 degrees 2-theta±0.2 degrees 2-theta, and also having any one, two, three or four additional peaks selected from 5.2, 14.6, 18.2 and 27.0 degrees 2-theta±0.2 degrees 2-theta.

Crystalline Form 5 of Asciminib may be alternatively characterized by an X-ray powder diffraction pattern having peaks at 5.2, 10.3, 14.6, 16.7, 18.2, 20.6, 24.9, and 27.0 degrees 2-theta±0.2 degrees 2-theta.

In one embodiment of the present disclosure, crystalline Form 5 of Asciminib is isolated.

Crystalline Form 5 of Asciminib may be heptane solvate. In embodiments, crystalline Form 5 of Asciminib may be a heptane solvate comprising: about 6 to about 12 wt %, about 7 to about 11 wt %, about 8 to about 10 wt %, about 8.5 to about 9.5 wt %, about 8.8 to about 9.3 wt % or about 9.1 wt % of heptane (e.g., as determined by GC analysis).

Crystalline Form 5 of Asciminib may be characterized by each of the above characteristics alone/or by all possible combinations, e.g., an XRPD pattern having peaks at 10.3, 16.7, 20.6 and 24.9 degrees 2-theta±0.2 degrees 2-theta; an XRPD pattern as depicted in FIG. 9, and combinations thereof.

The present disclosure includes a crystalline polymorph of Asciminib, designated Form 6. The crystalline Form 6 of Asciminib may be characterized by data selected from one or more of the following: an X-ray powder diffraction pattern substantially as depicted in FIG. 10 or 11; an X-ray powder diffraction pattern having peaks at 7.8, 12.5, 20.9 and 24.6 degrees 2-theta±0.2 degrees 2-theta; and combinations of these data.

Crystalline Form 6 of Asciminib may be further characterized by an X-ray powder diffraction pattern having peaks at 7.8, 12.5, 20.9 and 24.6 degrees 2-theta±0.2 degrees 2-theta, and also having any one, two, three or four additional peaks selected from 15.1, 19.3, 20.3 and 25.2 degrees 2-theta±0.2 degrees 2-theta.

Crystalline Form 6 of Asciminib may be alternatively characterized by an X-ray powder diffraction pattern having peaks at 7.8, 12.5, 15.1, 19.3, 20.3, 20.9, 24.6, and 25.2 degrees 2-theta±0.2 degrees 2-theta.

Crystalline Form 6 of Asciminib may be 2-methyl-THF and methyl ethyl ketone (MEK) solvates.

The crystalline Form 6 (2-methyl-THF solvate) of Asciminib may be characterized by data selected from one or more of the following: an X-ray powder diffraction pattern substantially as depicted in FIG. 10; an X-ray powder diffraction pattern having peaks at 7.8, 12.5, 20.9 and 24.6 degrees 2-theta±0.2 degrees 2-theta; and combinations of these data.

Crystalline Form 6 (2-methyl-THF solvate) of Asciminib may be further characterized by an X-ray powder diffraction pattern having peaks at 7.8, 12.5, 20.9 and 24.6 degrees 2-theta±0.2 degrees 2-theta, and also having any one, two, three or four additional peaks selected from 15.1, 19.3, 20.3 and 25.2 degrees 2-theta±0.2 degrees 2-theta.

Crystalline Form 6 (2-methyl-THF solvate) of Asciminib may be alternatively characterized by an X-ray powder diffraction pattern having peaks at 7.8, 12.5, 15.1, 19.3, 20.3, 20.9, 24.6, and 25.2 degrees 2-theta±0.2 degrees 2-theta.

In embodiments, crystalline Form 6 of Asciminib may be a 2-methyl-tetrahydrofuran (2-Me-THF) solvate comprising: about 6 to about 15 wt %, about 7 to about 13 wt %, about 8 to about 12 wt %, about 9 to about 11.5 wt %, about 10 to about 11 wt %, or about 10.5 wt % of 2-Me-THF (e.g., as determined by GC analysis). Optionally crystalline form 6 of Asciminib may be a hemi-2-methyl-tetrahydrofuran solvate.

The crystalline Form 6 (MEK solvate) of Asciminib may be characterized by data selected from one or more of the following: an X-ray powder diffraction pattern substantially as depicted in FIG. 11; an X-ray powder diffraction pattern having peaks at 7.8, 12.5, 20.9 and 24.6 degrees 2-theta±0.2 degrees 2-theta; and combinations of these data.

Crystalline Form 6 (MEK solvate) of Asciminib may be further characterized by an X-ray powder diffraction pattern having peaks at 7.8, 12.5, 20.9 and 24.6 degrees 2-theta±0.2 degrees 2-theta, and also having any one, two, three or four additional peaks selected from 15.1, 19.3, 20.3 and 25.2 degrees 2-theta±0.2 degrees 2-theta.

Crystalline Form 6 (MEK solvate) of Asciminib may be alternatively characterized by an X-ray powder diffraction pattern having peaks at 7.8, 12.5, 15.1, 19.3, 20.3, 20.9, 24.6, and 25.2 degrees 2-theta±0.2 degrees 2-theta, and also having any one, two, three or four additional peaks selected from and degrees 2-theta±0.2 degrees 2-theta.

In embodiments, crystalline Form 5 of Asciminib may be a methylethylketone (MEK) solvate comprising: about 4 to about 11 wt %, about 5 to about 10 wt %, about 6 to about 9 wt %, about 7 to about 8 wt %, or about 7.5 wt % of MEK (e.g., as determined by GC analysis). Optionally crystalline form 6 of Asciminib may be a hemi-methylethylketone solvate.

In one embodiment of the present disclosure, crystalline Form 6 of Asciminib is isolated.

Crystalline Form 6 of Asciminib may be characterized by each of the above characteristics alone/or by all possible combinations, e.g., an XRPD pattern having peaks at 7.8, 12.5, 20.9 and 24.6 degrees 2-theta±0.2 degrees 2-theta; an XRPD pattern as depicted in FIG. 10 or 11, and combinations thereof.

The present disclosure includes a crystalline polymorph of Asciminib, designated Form 7. The crystalline Form 7 of Asciminib may be characterized by data selected from one or more of the following: an X-ray powder diffraction pattern substantially as depicted in FIG. 12; an X-ray powder diffraction pattern having peaks at 5.5, 10.6, 11.5 and 18.1 degrees 2-theta±0.2 degrees 2-theta; and combinations of these data.

Crystalline Form 7 of Asciminib may be further characterized by an X-ray powder diffraction pattern having peaks at 5.5, 10.6, 11.5 and 18.1 degrees 2-theta±0.2 degrees 2-theta, and also having any one, two, three or four additional peaks selected from 13.8, 19.8, 26.2 and 27.9 degrees 2-theta±0.2 degrees 2-theta.

Crystalline Form 7 of Asciminib may be alternatively characterized by an X-ray powder diffraction pattern having peaks at 5.5, 10.6, 11.5, 13.8, 18.1, 19.8, 26.2, and 27.9 degrees 2-theta±0.2 degrees 2-theta.

In one embodiment of the present disclosure, crystalline Form 7 of Asciminib is isolated.

Crystalline Form 7 of Asciminib may be methyl isobutyl ketone (MIBK) solvate. Optionally, crystalline Form 7 of Asciminib may contain about 8 to about 12 wt % MIBK, or about 9 to about 11 wt % MIBK. Optionally crystalline form 7 of Asciminib may be a hemi-MIBK solvate.

Crystalline Form 7 of Asciminib may be characterized by each of the above characteristics alone/or by all possible combinations, e.g., an XRPD pattern having peaks at 5.5, 10.6, 11.5 and 18.1 degrees 2-theta±0.2 degrees 2-theta; an XRPD pattern as depicted in FIG. 12, and combinations thereof.

The present disclosure includes a crystalline polymorph of Asciminib hydrochloride.

The present disclosure includes a crystalline polymorph of Asciminib hydrochloride, designated Form A. The crystalline Form A of Asciminib hydrochloride may be characterized by data selected from one or more of the following: an X-ray powder diffraction pattern substantially as depicted in FIG. 2; an X-ray powder diffraction pattern having peaks at 12.6, 15.9, 17.0, 18.9 and 20.9 degrees 2-theta±0.2 degrees 2-theta; and combinations of these data.

Crystalline Form A of Asciminib hydrochloride may be further characterized by an X-ray powder diffraction pattern having peaks at 12.6, 15.9, 17.0, 18.9 and 20.9 degrees 2-theta±0.2 degrees 2-theta, and also having any one, two, three, four or five additional peaks selected from 11.8, 13.8, 16.5, 19.8 and 25.9 degrees 2-theta±0.2 degrees 2-theta.

Crystalline Form A of Asciminib hydrochloride may be alternatively characterized by an X-ray powder diffraction pattern having peaks at 11.8, 12.6, 13.8, 15.9, 16.5, 17.0, 18.9, 19.8, 20.9, and 25.9 degrees 2-theta±0.2 degrees 2-theta.

In one embodiment of the present disclosure, crystalline Form A of Asciminib hydrochloride is isolated.

Crystalline Form A of Asciminib hydrochloride may be anhydrous form.

Crystalline Form A of Asciminib hydrochloride may be characterized by each of the above characteristics alone or by all possible combinations, e.g., an XRPD pattern having peaks at 12.6, 15.9, 17.0, 18.9 and 20.9 degrees 2-theta±0.2 degrees 2-theta; an XRPD pattern as depicted in FIG. 2; and combinations thereof.

The present disclosure includes an amorphous form of Asciminib hydrochloride. The amorphous form of Asciminib hydrochloride may be characterized by an X-ray powder diffraction pattern substantially as depicted in FIG. 13.

The present disclosure includes a crystalline polymorph of Asciminib hydrochloride, designated Form B. The crystalline Form B of Asciminib hydrochloride may be characterized by data selected from one or more of the following: an X-ray powder diffraction pattern substantially as depicted in FIG. 14; an X-ray powder diffraction pattern having peaks at 7.2, 13.8, 22.7, 28.7 and 31.5 degrees 2-theta±0.2 degrees 2-theta; and combinations of these data.

Crystalline Form B of Asciminib hydrochloride may be further characterized by an X-ray powder diffraction pattern having peaks at 7.2, 13.8, 22.7, 28.7 and 31.5 degrees 2-theta #0.2 degrees 2-theta, and also having any one, two, three, four or five additional peaks selected from 14.3, 18.3, 21.3, 21.9 and 26.4 degrees 2-theta±0.2 degrees 2-theta.

Crystalline Form B of Asciminib hydrochloride may be alternatively characterized by an X-ray powder diffraction pattern having peaks at 7.2, 13.8, 14.3, 18.3, 21.3, 21.9, 22.7, 26.4 28.7, and 31.5 degrees 2-theta±0.2 degrees 2-theta.

In one embodiment of the present disclosure, crystalline Form B of Asciminib hydrochloride is isolated.

Crystalline Form B of Asciminib hydrochloride may be 1,4-dioxane solvate.

Crystalline Form B of Asciminib hydrochloride may be characterized by each of the above characteristics alone or by all possible combinations, e.g., an XRPD pattern having peaks at 7.2, 13.8, 22.7, 28.7 and 31.5 degrees 2-theta±0.2 degrees 2-theta; an XRPD pattern as depicted in FIG. 14; and combinations thereof.

The present disclosure includes a crystalline polymorph of Asciminib hydrochloride, designated Form C. The crystalline Form C of Asciminib hydrochloride may be characterized by data selected from one or more of the following: an X-ray powder diffraction pattern substantially as depicted in FIG. 15; an X-ray powder diffraction pattern having peaks at 9.2, 10.8, 18.0, 18.4 and 21.1 degrees 2-theta±0.2 degrees 2-theta; and combinations of these data.

Crystalline Form C of Asciminib hydrochloride may be further characterized by an X-ray powder diffraction pattern having peaks at 9.2, 10.8, 18.0, 18.4 and 21.1 degrees 2-theta±0.2 degrees 2-theta, and also having any one, two, three, four or five additional peaks selected from 15.5, 20.2, 21.7, 23.1 and 25.2 degrees 2-theta±0.2 degrees 2-theta.

Crystalline Form C of Asciminib hydrochloride may be alternatively characterized by an X-ray powder diffraction pattern having peaks at 9.2, 10.8, 15.5, 18.0, 18.4, 20.2, 21.1, 21.7, 23.1 and 25.2 degrees 2-theta±0.2 degrees 2-theta.

Crystalline Form C of Asciminib hydrochloride may alternatively or additionally be characterized by an XRPD pattern as depicted in FIG. 22.

Crystalline Form C of Asciminib hydrochloride may be substantially pure or in a mixture with crystalline Form A of Asciminib hydrochloride. Mixture of Form C and Form A of Asciminib hydrochloride may be characterized by an XRPD pattern as depicted in FIG. 15. Substantially pure Form C of Asciminib hydrochloride may be characterized by an XRPD substantially as depicted in FIG. 22.

The present disclosure includes a crystalline polymorph of Asciminib hydrobromide.

The present disclosure includes a crystalline polymorph of Asciminib hydrobromide, designated Form A. The crystalline Form A of Asciminib hydrobromide may be characterized by data selected from one or more of the following: an X-ray powder diffraction pattern substantially as depicted in FIG. 16; an X-ray powder diffraction pattern having peaks at 11.3, 15.9, 18.6, 24.2 and 24.9 degrees 2-theta±0.2 degrees 2-theta; and combinations of these data.

Crystalline Form A of Asciminib hydrobromide may be further characterized by an X-ray powder diffraction pattern having peaks at 11.3, 15.9, 18.6, 24.2 and 24.9 degrees 2-theta±0.2 degrees 2-theta, and also having any one, two, three, four or five additional peaks selected from 16.5, 17.7, 20.3, 23.0 and 30.3 degrees 2-theta±0.2 degrees 2-theta.

Crystalline Form A of Asciminib hydrobromide may be alternatively characterized by an X-ray powder diffraction pattern having peaks at 11.3, 15.9, 16.5, 17.7, 18.6, 20.3, 23.0, 24.2, 24.9 and 30.3 degrees 2-theta±0.2 degrees 2-theta.

In embodiments, crystalline Form A of Asciminib hydrobromide may be alternatively or additionally characterized by FTIR peaks at: 3395, 1659, 1149 and 1027±4 cm-1; or by a FTIR spectrum substantially as depicted in FIG. 20.

In one embodiment of the present disclosure, crystalline Form A of Asciminib hydrobromide is isolated.

Crystalline Form A of Asciminib hydrobromide may be anhydrous form.

Crystalline Form A of Asciminib hydrobromide may be characterized by each of the above characteristics alone or by all possible combinations, e.g., an XRPD pattern having peaks at 11.3, 15.9, 18.6, 24.2 and 24.9 degrees 2-theta±0.2 degrees 2-theta; an XRPD pattern as depicted in FIG. 16; and combinations thereof.

The present disclosure includes a crystalline polymorph of Asciminib mesylate.

The present disclosure includes a crystalline polymorph of Asciminib mesylate, designated Form A. The crystalline Form A of Asciminib mesylate may be characterized by data selected from one or more of the following: an X-ray powder diffraction pattern substantially as depicted in FIG. 17; an X-ray powder diffraction pattern having peaks at 8.9, 18.9, 19.6, 23.7 and 25.4 degrees 2-theta±0.2 degrees 2-theta; and combinations of these data.

Crystalline Form A of Asciminib mesylate may be further characterized by an X-ray powder diffraction pattern having peaks at 8.9, 18.9, 19.6, 23.7 and 25.4 degrees 2-theta±0.2 degrees 2-theta, and also having any one, two, three, four or five additional peaks selected from 7.9, 14.5, 20.5, 21.2 and 24.4 degrees 2-theta±0.2 degrees 2-theta.

Crystalline Form A of Asciminib mesylate may be alternatively characterized by an X-ray powder diffraction pattern having peaks at 7.9, 8.9, 14.5, 18.9, 19.6, 20.5, 21.2, 23.7, 24.4, and 25.4 degrees 2-theta±0.2 degrees 2-theta.

Asciminib mesylate form A can be characterized by FTIR peaks at: 3284, 1677, 1633 and 1051±4 cm 1; or by a FTIR spectrum substantially as depicted in FIG. 21.

In one embodiment of the present disclosure, crystalline Form A of Asciminib mesylate is isolated.

Crystalline Form A of Asciminib mesylate may be anhydrous form.

Crystalline Form A of Asciminib mesylate may be characterized by each of the above characteristics alone or by all possible combinations, e.g., an XRPD pattern having peaks at 8.9, 18.9, 19.6, 23.7 and 25.4 degrees 2-theta±0.2 degrees 2-theta; an XRPD pattern as depicted in FIG. 17; and combinations thereof.

The present disclosure includes a crystalline polymorph of Asciminib phosphate.

The present disclosure includes a crystalline polymorph of Asciminib phosphate, designated Form A. The crystalline Form A of Asciminib phosphate may be characterized by data selected from one or more of the following: an X-ray powder diffraction pattern substantially as depicted in FIG. 18; an X-ray powder diffraction pattern having peaks at 9.9, 11.5, 11.9, 13.7 and 14.4 degrees 2-theta±0.2 degrees 2-theta; and combinations of these data.

Crystalline Form A of Asciminib phosphate may be further characterized by an X-ray powder diffraction pattern having peaks at 9.9, 11.5, 11.9, 13.7 and 14.4 degrees 2-theta±0.2 degrees 2-theta, and also having any one, two, three, four or five additional peaks selected from 6.9, 7.2, 20.3, 21.5 and 23.5 degrees 2-theta±0.2 degrees 2-theta.

Crystalline Form A of Asciminib phosphate may be alternatively characterized by an X-ray powder diffraction pattern having peaks at 6.9, 7.2, 9.9, 11.5, 11.9, 13.7, 14.4, 20.3, 21.5, and 23.5 degrees 2-theta±0.2 degrees 2-theta.

In one embodiment of the present disclosure, crystalline Form A of Asciminib phosphate is isolated.

Crystalline Form A of Asciminib phosphate may be characterized by each of the above characteristics alone or by all possible combinations, e.g., an XRPD pattern having peaks at 9.9, 11.5, 11.9, 13.7 and 14.4 degrees 2-theta±0.2 degrees 2-theta; an XRPD pattern as depicted in FIG. 18; and combinations thereof.

The present disclosure includes a crystalline polymorph of Asciminib sulphate.

The present disclosure includes a crystalline polymorph of Asciminib sulphate, designated Form A. The crystalline Form A of Asciminib sulphate may be characterized by data selected from one or more of the following: an X-ray powder diffraction pattern substantially as depicted in FIG. 19; an X-ray powder diffraction pattern having peaks at 7.6, 10.1, 13.5, 15.4 and 20.2 degrees 2-theta±0.2 degrees 2-theta; and combinations of these data.

Crystalline Form A of Asciminib sulphate may be further characterized by an X-ray powder diffraction pattern having peaks at 7.6, 10.1, 13.5, 15.4 and 20.2 degrees 2-theta±0.2 degrees 2-theta, and also having any one, two, three, four or five additional peaks selected from 6.7, 10.6, 21.7, 23.2 and 27.1 degrees 2-theta±0.2 degrees 2-theta.

Crystalline Form A of Asciminib sulphate may be alternatively characterized by an X-ray powder diffraction pattern having peaks at 7.6, 10.1, 13.5, 15.4 and 20.2 degrees 2-theta±0.2 degrees 2-theta, and also having any one, two, three, four or five additional peaks selected from 6.7, 10.6, 21.7, 23.2 and 27.1 degrees 2-theta±0.2 degrees 2-theta.

In one embodiment of the present disclosure, crystalline Form A of Asciminib sulphate is isolated.

Crystalline Form A of Asciminib sulphate may be characterized by each of the above characteristics alone or by all possible combinations, e.g., an XRPD pattern having peaks at 7.6, 10.1, 13.5, 15.4 and 20.2 degrees 2-theta±0.2 degrees 2-theta; an XRPD pattern as depicted in FIG. 19; and combinations thereof.

The above crystalline polymorphs can be used to prepare other crystalline polymorphs of Asciminib, Asciminib salts and their solid state forms.

The present disclosure encompasses a process for preparing other solid state forms of Asciminib, Asciminib salts and their solid state forms thereof. The process includes preparing any one of the Asciminib (salts) and solid state forms of Asciminib by the processes of the present disclosure, and converting it to other Asciminib salt.

The present disclosure provides the above described crystalline polymorphs of Asciminib for use in the preparation of pharmaceutical compositions comprising Asciminib and/or crystalline polymorphs thereof. In particular the present disclosure encompasses the use of the above described solid state forms of Asciminib and salts thereof, for the preparation of a pharmaceutical composition in the form of a solid dispersion comprising Asciminib or salt thereof.

The present disclosure also encompasses the use of crystalline polymorphs of Asciminib and salts thereof of the present disclosure for the preparation of pharmaceutical compositions of Asciminib and salts thereof and/or crystalline polymorphs thereof. In particular the present disclosure encompasses the above described solid state forms of Asciminib and salts thereof, for the preparation of a pharmaceutical composition or formulation, preferably an oral formulation in the form of a solid dispersion comprising Asciminib or salt thereof.

The present disclosure includes processes for preparing the above mentioned pharmaceutical compositions. The processes include combining any one or a combination of the crystalline polymorphs of Asciminib and salts thereof of the present disclosure with at least one pharmaceutically acceptable excipient. The process may alternatively further comprise combining any one or a combination of the crystalline polymorphs of Asciminib and salts thereof of the present disclosure with one or more pharmaceutically acceptable excipients, preferably one or more polymeric carriers, to obtain a solid dispersion or premix comprising amorphous Asciminib, and optionally further comprising combining the solid dispersion or premix with one or more further pharmaceutically acceptable excipients to form a pharmaceutical composition or pharmaceutical formulation comprising the solid dispersion.

The present disclosure further provides pharmaceutical compositions comprising the solid state forms of Asciminib and salts thereof, or combinations thereof, according to the present disclosure. Said pharmaceutical compositions may comprise a premix of at least one of the above solid state forms. The premix may be, for example, in a form of solid solution or solid dispersion.

Pharmaceutical combinations or formulations of the present disclosure contain any one or a combination of the solid state forms of Asciminib and salts thereof of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Asciminib and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Asciminib can be administered. Asciminib may be formulated for administration to a mammal, in embodiments to a human, by injection. Asciminib can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Asciminib and salts thereof and the pharmaceutical compositions and/or formulations of Asciminib of the present disclosure can be used as medicaments, in embodiments in the treatment of Chronic Myeloid Leukemia (CML) and Philadelphia chromosome-positive acute lymphoblastic leukemia.

The present disclosure also provides methods of treating Chronic Myeloid Leukemia (CML) and Philadelphia chromosome-positive acute lymphoblastic leukemia by administering a therapeutically effective amount of any one or a combination of the crystalline polymorphs of Asciminib of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector. Scanning parameters: angle range: 3-40 deg., step size 0.0167, time per step 37 s, continuous scan.

Fourier-Transform Infrared Spectroscopy ("FTIR")

FTIR spectra were recorded on a Nicolet 6700 interferometer between 4000 $cm^{-1}$ and 370 $cm^{-1}$ with resolution of 4 $cm^{-1}$, in KBr technique.

Gas Chromatography ("GC")

GC data is obtained on Agilent 7890A or equivalent instrument with FID detector on a column DB-624, 30 m×0.53 mm, 3 μm.

EXAMPLES

Preparation of Starting Materials

Asciminib can be prepared according to methods known from the literature, for example U.S. Pat. No. 8,829,195.

Example 1: Preparation of Asciminib Form 1

Asciminib (0.25 grams) was dissolved in 2-propanol (2.2 mL) at about 65° C. The solution was cooled to RT (about 25° C.) and crystallization occurred during cooling at about 29° C. Reaction mixture was stirred at RT for 1 hour, cooled to about 0° C. and stirred for 30 min. The precipitate was filtered and analyzed by XRPD. Asciminib Form 1, was obtained.

Example 2: Preparation of Asciminib hydrochloride Form A

Asciminib (0.5 grams) was dissolved in 2-propanol (5 mL) at about 60° C. and hydrochloric acid in 2-propanol (0.2 mL; 5-6 M) was added in one portion. The reaction mixture was stirred at 60° C. for 30 minutes, cooled down to room temperature (RT) and stirred for 16 hours. The precipitate was filtered and analyzed by XRPD (FIG. 1). Asciminib hydrochloride Form A was obtained.

Example 3: Preparation of Asciminib Hydrochloride Form A

Asciminib (2 grams) was dissolved in ethyl acetate (98 mL) at about 70° C. and hydrochloric acid, conc. (36.5%, 0.2 mL) solution in ethyl acetate (10 mL) was added drop wise. The reaction mixture was stirred at 70° C. for 30 minutes, cooled to RT and stirred for 16 hours. The precipitate was filtered and analyzed by XRPD. Asciminib hydrochloride Form A was obtained.

Example 4: Preparation of Asciminib Amorphous Form

Asciminib (2.0 grams) was dissolved in methanol (80 mL) at room temperature (RT). Solvent was removed by vacuum evaporation (10 mbar) at 50° C. Obtained solid was analyzed by XRPD. Asciminib amorphous form was obtained.

Example 5: Preparation of Asciminib Form 2

Asciminib (0.25 grams) was dissolved in 1,4-dioxane (4 mL) at about 60° C. and the obtained solution cooled down to room temperature. Crystallization occurred and the obtained suspension was stirred at room temperature for 1 hour. The precipitate was filtered and analyzed by XRPD. Asciminib Form 2 was obtained.

Example 6: Preparation of Asciminib Form 2

Asciminib amorphous (20 mg) was exposed to vapors of 1,4-dioxane (4 mL) for 7 days at room temperature. Resulting solid was analyzed by XRPD. Asciminib Form 2 was obtained.

Example 7: Preparation of Asciminib Form 3

Asciminib (0.25 grams) was dissolved in 1-propanol (2 mL) at about 70° C. The solution was cooled down to room temperature and crystallization occurred during cooling, at about 44° C. Obtained suspension was stirred at room temperature for 1 hour. The precipitate was filtered and analyzed by XRPD. Asciminib Form 3 (1-propanol solvate) was obtained.

Example 8: Preparation of Asciminib Form 3

Asciminib amorphous (20 mg) was exposed to vapors of 1-propanol (4 mL) for 7 days at room temperature. Resulting solid was analyzed by XRPD. Asciminib Form 3 (1-propanol solvate) was obtained.

Example 9: Preparation of Asciminib Form 3

Suspension of Asciminib amorphous (0.10 grams) in 1-propanol (1 mL) was stirred for 3 days at room temperature. Solid was filtered and analyzed by XRPD. Asciminib Form 3 (1-propanol solvate) was obtained.

Example 10: Preparation of Asciminib Form 3

Asciminib amorphous (20 mg) was exposed to vapors of 1-BuOH (4 mL) for 10 days at room temperature. Resulting solid was analyzed by XRPD. Asciminib Form 3 (1-butanol solvate) was obtained.

Example 11: Preparation of Asciminib Form 3

Asciminib (0.26 grams) was dissolved in 1-butanol (2 mL) at about 80° C. The solution was cooled down to room temperature and crystallization occurred during cooling, at about 44° C. Obtained suspension was stirred at room temperature for 1 hour. The precipitate was filtered and analyzed by XRPD. Asciminib Form 3 (1-butanol solvate) was obtained.

Example 12: Preparation of Asciminib Form 3

Asciminib amorphous (20 mg) was exposed to vapors of i-BuOH (4 mL) for 10 days at room temperature. Resulting solid was analyzed by XRPD. Asciminib Form 3 (i-butanol solvate) was obtained.

Example 13: Preparation of Asciminib Form 4

Asciminib (0.25 grams) was dissolved in methanol/water 9:1 (1.5 mL) at about 55° C. The solution was cooled down to room temperature and stirred for 16 hours. Obtained solid was filtered and analyzed by XRPD. Asciminib Form 4 was obtained.

Example 14: Preparation of Asciminib Form 4

Asciminib amorphous (20 mg) was exposed to vapors of methanol (4 mL) for 7 days at room temperature. Solid was analyzed by XRPD. Asciminib Form 4 was obtained.

Example 15: Preparation of Asciminib Form 5

Asciminib (20 mg) was dissolved in methanol (2 mL) at room temperature. Heptane (2 mL) was added drop wise to the solution and the obtained suspension was stirred at room temperature for 16 hours. The precipitate was filtered and analyzed by XRPD. Asciminib Form 5 was obtained.

Example 16: Preparation of Asciminib Form 5

Asciminib amorphous (20 mg) was exposed to vapors of heptane (4 mL) for 7 days at room temperature. Solid was analyzed by XRPD. Asciminib Form 5 was obtained.

Example 17: Preparation of Asciminib Form 6

Asciminib (0.25 grams) was dissolved in 2-methyl-THF (11 mL) at about 60° C. The solution was cooled down to room temperature and stirred for 16 hours. Obtained solid was filtered and analyzed by XRPD. Asciminib Form 6 (2-methyl-THF solvate) was obtained.

Example 18: Preparation of Asciminib Form 6

Asciminib amorphous (20 mg) was exposed to vapors of 2-methyl-THF (4 mL) for 7 days at room temperature. Solid was analyzed by XRPD. Asciminib Form 6 (2-methyl-THF solvate) was obtained.

Example 19: Preparation of Asciminib Form 6

Asciminib amorphous (0.10 grams) suspension in 2-methyl-THF (1 mL) was stirred for 3 days at room temperature. Solid was filtered and analyzed by XRPD. Asciminib Form 6 (2-methyl-THF solvate) was obtained.

Example 20: Preparation of Asciminib Form 6

Asciminib amorphous (50 mg) suspension in MEK (1 mL) was stirred for 3 days at room temperature. Obtained solid was filtered and analyzed by XRPD. Asciminib Form 6 (MEK solvate) was obtained.

Example 21: Preparation of Asciminib Form 7

Asciminib (0.25 grams) was dissolved in MIBK (11 mL) at about 60° C. The solution was cooled down to room temperature and stirred for 16 hours. Obtained solid was filtered and analyzed by XRPD. Asciminib Form 7 was obtained.

Example 22: Preparation of Asciminib Form 7

Asciminib amorphous (0.10 grams) suspension in MIBK (1 mL) was stirred for 7 days at room temperature. Solid was filtered and analyzed by XRPD. Asciminib Form 7 was obtained.

Example 23: Preparation of Asciminib Hydrochloride Amorphous Form

Asciminib HCl (0.50 grams) was dissolved in methanol (20 mL) at room temperature. Solvent was removed by vacuum evaporation (10 mbar) at 50° C. Remained solid was analyzed by XRPD. Amorphous Asciminib HCl was obtained.

Example 24: Preparation of Asciminib Hydrochloride Form B

Amorphous Asciminib hydrochloride (1.0 grams) was weighed into 25 mL round bottomed flask, equipped with condenser and magnetic stirrer. 1,4-dioxane (10 mL) was added and the suspension was stirred at about 25° C. for 1 hour. The solid was filtered and analyzed by XRPD. Asciminib hydrochloride Form B was obtained.

Example 25: Preparation of Asciminib Hydrochloride Form C

Asciminib hydrochloride Form B (0.9 grams) was weighed into 25 mL round bottomed flask, equipped with condenser and magnetic stirrer. Heptane (10 mL) was added and the suspension was heated up to about 100° C. and stirred for 30 minutes. The solid was filtered and analyzed by XRPD. Asciminib hydrochloride Form C in a mixture with Form A was obtained.

Example 26: Preparation of Asciminib Hydrobromide Form A

Asciminib (1.0 grams) was weighed into 50 mL round bottomed flask, equipped with condenser and magnetic stirrer. Ethanol (14 mL) and ethyl acetate (14 mL) were added and the suspension was heated to about 70° C. Clear solution was obtained. Hydrobromic acid aqueous, 47% (0.13 mL) was added drop wise to the Asciminib solution and the reaction mixture was stirred for 30 minutes at 70° C., cooled to room temperature and stirred for 24 hours. Ethyl acetate (10 mL) was added drop wise to the solution. Obtained suspension was stirred for additional 30 minutes at room temperature. The solid was filtered and analyzed by XRPD. Asciminib hydrobromide Form A was obtained.

Example 27: Preparation of Asciminib Mesylate Form A

Asciminib (1.0 grams) was weighed into 50 mL round bottomed flask, equipped with condenser and magnetic stirrer. Ethanol (3 mL) and ethyl acetate (10 mL) were added and the suspension was heated to about 70° C. Clear solution was obtained. Methanesulfonic acid (0.173 mL) was added in one portion to the Asciminib solution and the reaction mixture was stirred for 30 minutes at 70° C. The solution was cooled to room temperature and stirred for 24 hours. The solid was filtered and analyzed by XRPD. Asciminib mesylate Form A was obtained.

Example 28: Preparation of Asciminib Phosphate Form A

Asciminib (1.0 grams) was weighed into 50 mL round bottomed flask, equipped with condenser and magnetic stirrer. Ethanol (3 mL) and ethyl acetate (10 mL) were added and the suspension was heated to about 70° C. Clear solution was obtained.

Phosphoric acid aqueous, 85% (0.153 mL) was added drop wise with ethyl acetate (4 mL) and ethanol (1 mL) to the Asciminib solution and the reaction mixture was stirred for 30 minutes at 70° C. The solution was cooled to room temperature and stirred for 16 hours. The solid was filtered and analyzed by XRPD. Asciminib phosphate Form A was obtained.

Example 29: Preparation of Asciminib Sulphate Form A

Asciminib (1.0 grams) was weighed into 50 mL round bottomed flask, equipped with condenser and magnetic stirrer. Ethanol (3 mL) and ethyl acetate (10 mL) were added and the suspension was heated to about 70° C. Clear solution was obtained.

Sulphuric acid aqueous, 96% (0.142 mL) was added drop wise with ethyl acetate (4 mL) and ethanol (1 mL) to the Asciminib solution and the reaction mixture was stirred for 30 minutes at 70° C. The solution was cooled to room temperature and stirred for 16 hours. The solid was filtered and analyzed by XRPD. Asciminib sulphate Form A was obtained.

Example 30: Preparation of Asciminib Hydrochloride Form C

Asciminib hydrochloride Form B (0.9 grams) was weighed into 25 mL round bottomed flask, equipped with condenser and magnetic stirrer. Heptane (10 mL) was added and the suspension was heated up to about 100° C. and stirred for 30 minutes. The solid was filtered and analyzed by XRPD. Asciminib hydrochloride Form C was obtained (FIG. 22).

The invention claimed is:

1. A crystalline form of Asciminib mesylate, which is characterized by data selected from:
a. an XRPD pattern having peaks at 8.9, 18.9, 19.6, 23.7 and 25.4 degrees 2-theta±0.2 degrees 2-theta; and
b. an XRPD pattern substantially as depicted in FIG. 17.

2. The crystalline form of Asciminib mesylate according to claim 1, which is further characterized by data selected from:
c. an X-ray powder diffraction pattern having peaks at 8.9, 18.9, 19.6, 23.7 and 25.4 degrees 2-theta±0.2 degrees 2-theta, and also having any one, two, three, four or five additional peaks selected from 7.9, 14.5, 20.5, 21.2 and 24.4 degrees 2-theta±0.2 degrees 2-theta;
d. a solid state FTIR spectrum having peaks at: 3284, 1677, 1633 and 1051±4 $cm^{-1}$;
e. a solid state FTIR spectrum substantially as depicted in FIG. 21; and
f. combinations of any two or more of c), d) or e).

3. The crystalline form of Asciminib mesylate according to claim 1, which is characterized by an XRPD pattern having peaks at 7.9, 8.9, 14.5, 18.9, 19.6, 20.5, 21.2, 23.7, 24.4, and 25.4 degrees 2-theta±0.2 degrees 2-theta.

4. The crystalline form of Asciminib mesylate according to claim 1, wherein the crystalline form is anhydrous.

5. The crystalline form of Asciminib mesylate according to claim 1, which contains no more than about 20% of any other crystalline forms of Asciminib mesylate.

6. The crystalline form of Asciminib mesylate according to claim 1, which contains no more than about 20% of amorphous Asciminib mesylate.

7. A pharmaceutical composition comprising the crystalline form of Asciminib mesylate according to claim 1 in an undissolved state.

8. A pharmaceutical formulation comprising the crystalline form of Asciminib mesylate according to claim 1 in an undissolved state, with at least one pharmaceutically acceptable excipient.

9. A process for preparing a pharmaceutical formulation, comprising combining the crystalline form of Asciminib mesylate according to claim 1 in an undissolved state, with at least one pharmaceutically acceptable excipient.

10. A method of treating chronic myeloid leukemia or Philadelphia chromosome-positive acute lymphoblastic leukemia, comprising administering a therapeutically effective amount of the crystalline form of Asciminib mesylate according to claim 1 to a subject in need of the treatment.

* * * * *